(12) United States Patent
Gerlach et al.

(10) Patent No.: US 6,774,136 B2
(45) Date of Patent: Aug. 10, 2004

US006774136B2

(54) SUBSTITUTED 1 AND 2 NAPHTHOL MANNICH BASES

(75) Inventors: Matthias Gerlach, Brachttal (DE); Corinna Maul, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/149,449

(22) PCT Filed: Dec. 20, 2000

(86) PCT No.: PCT/EP00/12972

§ 371 (c)(1),
(2), (4) Date: Jun. 27, 2002

(87) PCT Pub. No.: WO01/47866

PCT Pub. Date: Jul. 5, 2001

(65) Prior Publication Data

US 2004/0044061 A1 Mar. 4, 2004

(30) Foreign Application Priority Data

Dec. 27, 1999 (DE) ......................... 199 63 179

(51) Int. Cl.[7] ............................................ A61K 31/445
(52) U.S. Cl. ...................... 514/319; 514/428; 546/206; 548/570
(58) Field of Search ................................ 514/319, 428; 546/206; 548/570

(56) References Cited

FOREIGN PATENT DOCUMENTS

| EP | 0 864 559 | 9/1998 |
|---|---|---|
| WO | 96 22276 | 7/1996 |

OTHER PUBLICATIONS

Kartritzky et al., 1999, J. Org. Chem., 64:6071–6075.*
Katritzky et al., 1999, CA:131:243022.*
Fateen et al., 1972, Egypt. J. Chem., 15(4):329–336.*
Fateen et al., 1972, CA:80:108438.*
C. Cardellicchio et al.: "The Betti base: absolute configuration and routes to a family of related chiral nonracemic bases" Tetrahedron: Asymmetry, vol. 9, No. 20, pp. 3667–3675 Oct. 23, 1998.
A. R. Katritzky, et al., J. Org. Chem., vol. 64, pp. 6071–6075, "Amino(Hetero)Arylmethylation of Phenols with N–[α–Amino(Hetero) Arylmethyl] Benzotriazoles", 1999.
L. C. Hendershot, et al., J. Pharmacol. Exp. Ther., vol. 125, pp. 237–240, "Antagonism of the Frequency of Phenylquinone–Induced Writhing in the Mouse by Weak Analgesics and Nonanalgesics", 1959.
M. Picardo, et al., High Throughput Screening: The Discovery of Bioactive Substances, pp. 307–316, "Scintillation Proximity Assays".
O. Jeanneton, et al., The Journal of Pharmacology and Experimental Therapeutics, vol. 267, No. 1, pp. 31–37, "Platelet–Activating Factor (PAF) Induces a Contraction of Isolated Smooth Muscle Cells From Guinea Pig Ileum: Intracellular Pathway Involved", 1993.
M. CH. Frink, et al., Arzneim–Forsch./Drug Res., vol. 46, No. 11, pp. 1029–1036, "Influence of Tramadol on Neurotransmitter Systems of the Rat Brain", 1996.
E. G. Gray, et al., J. Anat., vol. 76, pp. 79–88, "The Isolation of Nerve Endings From Brain: An Electron–Microscopic Study of Cell Fragments Derived by Homogenization and Centrifugation", 1962.

* cited by examiner

Primary Examiner—Joseph K. McKane
Assistant Examiner—Robert Shiao
(74) Attorney, Agent, or Firm—Oblon, Spivak, McClelland, Maier & Neustadt, P.C.

(57) ABSTRACT

The invention relates to substituted 1 and 2 naphthol Mannich bases, a method for the production thereof, medicaments containing said compounds and the use of said compounds in the production of medicaments.

113 Claims, 2 Drawing Sheets

SUBSTITUTED 1 AND 2 NAPHTHOL MANNICH BASES

This application is a 371 of PCT/EP02/12972, filed on Dec. 20, 2000.

BACKGROUND OF THE INVENTION

1. Field of the Invention

The invention relates to substituted 1- and 2-naphthol Mannich bases, processes for their preparation, medicaments comprising these compounds and the use of these compounds for the preparation of medicaments.

2. Description of the Background

Pain is one of the basic clinical symptoms. There is a worldwide need for effective pain treatments. The urgent need for action for target-orientated treatment of chronic and non-chronic states of pain appropriate for the patient, by which is to be understood successful and satisfactory pain treatment for the patient, is documented in the large number of scientific works which have been published in the field of applied analgesia and basic research in nociception in recent years.

Conventional opioids, such as e.g. morphine, are effective in the treatment of severe to very severe pain. However, they have as undesirable concomitant symptoms, inter alia, respiratory depression, vomiting, sedation, constipation and development of tolerance.

Tramadol hydrochloride-(1RS,2RS)-2-[(dimethylamino) methyl]-1-(3-methoxyphenyl)-cyclohexanol—occupies a special position among analgesics having an action on the central nervous system, since this active compound brings about potent inhibition of pain without the side effects known of opioids (J. Pharmacol. Exptl. Ther. 267, 33 (1993)). Research is being conducted worldwide into further pain-inhibiting agents.

The object of the present invention was therefore to provide new compounds which are suitable in particular as active compounds in medicaments.

These active compounds should be suitable in particular for pain treatment and for treatment of inflammatory and allergic reactions, drug and/or alcohol abuse, diarrhoea, gastritis, ulcers, cardiovascular diseases, urinary incontinence, depression, states of shock, migraines, narcolepsy, excess weight, asthma, glaucoma and/or hyperkinetic syndrome.

SUMMARY OF THE INVENTION

This object is achieved according to the invention by providing substituted 1- and 2-naphthol Mannich bases of the following general formula I which have a pronounced analgesic action and which moreover are suitable for treatment of/combating inflammatory and allergic reactions, drug and/or alcohol abuse, diarrhoea, gastritis, ulcers, cardiovascular diseases, urinary incontinence, depression, states of shock, migraines, narcolepsy, excess weight, asthma, glaucoma and/or hyperkinetic syndrome.

The invention therefore provides substituted 1- and 2-naphthol Mannich bases of the general formula I

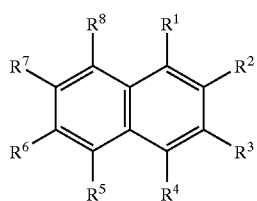

wherein $R^1=CH(R^9)N(R^{10})(R^{11})$ and $R^2=OR^{12}$ or $R^1=OR^{12}$ and $R^2=CH(R^9)N(R^{10})(R^{11})$, and in each case the radicals $R^3$ to $R^8$ are identical or different and=H, F, Cl, Br, $CF_3$, CN, $NO_2$, $SO_2NH_2$, $SO_2NHR^{13}$, $NHR^{13}$, $SR^{15}$, $OR^{16}$, $CO(OR^{20})$, $CH_2CO(OR^{21})$, $CO(R^{22})$, a $C_{1-10}$-alkyl, an aryl or a heteroaryl radical or an aryl or heteroaryl radical bonded via a $C_{1-6}$-alkylene group, preferably= H, F, Cl, Br, $SO_2NH_2$, $NHR^{13}$, $CO(R^{22})$, $OR^{16}$, $CO(OR^{20})$, a $C_{1-6}$-alkyl radical or an aryl radical bonded via a $C_{1-2}$-alkylene group, particularly preferably H, $NHR^{13}$, $CO(R^{22})$, $OR^{16}$ or $CO(OR^{20})$, $R^9$ denotes an aryl radical, a heteroaryl radical or an alkyl radical without an acid proton in the α-position, preferably an unsubstituted phenyl radical or a phenyl radical which is at least monosubstituted by $C_{1-4}$-alkyl, $C_{1-3}$-alkoxy, halogen, $CF_3$, CN, O-phenyl or OH, particularly preferably an unsubstituted phenyl radical or a 2-methoxy-phenyl, 3-methoxy-phenyl, 4-methoxy-phenyl, 2-methyl-phenyl, 3-methyl-phenyl, 4-methyl-phenyl, 2-tert-butyl-phenyl, 3-tert-butyl-phenyl, 4-tert-butyl-phenyl, 2-fluoro-phenyl, 3-fluoro-phenyl, 4-fluoro-phenyl, 2-chloro-phenyl, 3-chloro-phenyl, 4-chloro-phenyl, 2-bromo-phenyl, 3-bromo-phenyl, 4-bromo-phenyl, 5-bromo-2-fluoro-phenyl, 2-chloro-4-fluoro-phenyl, 2-chloro-5-fluoro-phenyl, 2-chloro-6-fluoro-phenyl, 4-bromo-2-fluoro-phenyl, 3-bromo-4-fluoro-phenyl, 3-bromo-2-fluoro-phenyl, 2,3-dichloro-phenyl, 2,4-dichloro-phenyl, 2,5-dichlorophenyl, 3,4-dichloro-phenyl, 2,3-dimethyl-phenyl, 2,4-dimethyl-phenyl, 2,5-dimethylphenyl, 2,3-dimethoxy-phenyl, 2,4-dimethoxy-phenyl, 2,5-dimethoxy-phenyl, 3,4-dimethoxy-phenyl, 3,4,5-trimethoxy-phenyl, 2-trifluoromethyl-phenyl, 3-trifluoromethyl-phenyl or 4-trifluoromethyl-phenyl radical, very particularly preferably an unsubstituted phenyl radical, $R^{10}$, $R^{11}$ are identical or different and denote a branched or unbranched, saturated or unsaturated, unsubstituted or at least monosubstituted $C_{1-6}$-alkyl radical or an unsubstituted or at least monosubstituted phenyl, benzyl or phenethyl radical, preferably a saturated, unsubstituted or at least monosubstituted $C_{1-6}$-alkyl radical, particularly preferably a $CH_3$ radical, or $R^{10}$ and $R^{11}$ together denote $(CH_2)_n$, where n=an integer from 3 to 6, or $(CH_2)_2O(CH_2)_2$, preferably $(CH_2)_n$, where n=4 or 5, $R^{12}$=H, $COR^{22}$, a $C_{1-10}$-alkyl, an aryl or a heteroaryl radical or an aryl or heteroaryl radical bonded via a $C_{1-6}$-alkylene group, preferably=H, a $C_{1-6}$-alkyl radical or an aryl radical bonded via a $C_{1-2}$-alkylene group, $R^{13}$=H, $COR^{14}$, a $C_{1-10}$-alkyl, an aryl or a heteroaryl radical or an aryl or heteroaryl radical bonded via a $C_{1-6}$-alkylene group, preferably=H, a $C_{1-6}$-alkyl radical or an aryl radical bonded via a $C_{1-2}$-alkylene group, particularly preferably=H, $R^{14}$=H, a $C_{1-10}$-alkyl, an aryl or a heteroaryl radical or an aryl or heteroaryl radical bonded via a $C_{1-6}$-alkylene group, preferably a $C_{1-6}$-alkyl radical or an aryl radical bonded via a $C_{1-2}$-alkylene group, $R^{15}$=H, a $C_{1-10}$-alkyl, an aryl or a heteroaryl radical or an aryl or heteroaryl radical bonded via a $C_{1-6}$-alkylene group, preferably a $C_{1-6}$-alkyl radical or an aryl radical bonded via a $C_{1-2}$-alkylene group, $R^{16}$=H, CO($R^{17}$), a $C_{1-10}$-alkyl, an aryl or a heteroaryl radical or an aryl or heteroaryl radical bonded via a $C_{1-6}$-alkylene group, preferably H, a $C_{1-6}$-alkyl radical, an aryl radical bonded via a $C_{1-2}$-alkylene group or CO($R^{17}$), particularly preferably H or CO($R^{17}$), $R^{17}$=H, a $C_{1-10}$-alkyl, an aryl or a heteroaryl radical or an aryl or heteroaryl radical bonded via a $C_{1-6}$-alkylene group, preferably a $C_{1-6}$-alkyl radical, an aryl radical bonded via a $C_{1-2}$-alkylene group or a phenyl radical which is optionally substituted by F, Cl, Br, $C_{1-4}$-alkyl or $C_{1-3}$-alkoxy, particularly preferably a phenyl radical which is optionally substituted by F, Cl, Br, $C_{1-4}$-alkyl or $C_{1-3}$-alkoxy, $R^{18}$=H, a $C_{1-10}$-alkyl, an aryl or a heteroaryl radical or an aryl or heteroaryl radical bonded via a $C_{1-6}$-alkylene group, preferably a $C_{1-6}$-alkyl radical, an aryl radical bonded via a $C_{1-2}$-alkylene group or a phenyl or naphthyl radical which is optionally substituted by F, Cl, Br, $C_{1-4}$-alkyl or $C_{1-3}$-alkoxy, particularly preferably a phenyl radical which is optionally substituted by F, Cl, Br, $C_{1-4}$-alkyl or $C_{1-3}$-alkoxy, $R^{20}$=H, a $C_{1-10}$-alkyl, an aryl or a heteroaryl radical or an aryl or heteroaryl radical bonded via a $C_{1-6}$-alkylene group, preferably H, a $C_{1-6}$-alkyl radical, an aryl radical bonded via a $C_{1-2}$-alkylene group or a phenyl radical which is optionally substituted by F, Cl, Br, $C_{1-4}$-alkyl or $C_{1-3}$-alkoxy, particularly preferably H or a phenyl radical which is optionally substituted by F, Cl, Br, $C_{1-4}$-alkyl or $C_{1-3}$-alkoxy, $R^{21}$=H, a $C_{1-10}$-alkyl, an aryl or a heteroaryl radical or an aryl or heteroaryl radical bonded via a $C_{1-6}$-alkylene group, preferably=H, a $C_{1-6}$-alkyl radical or an aryl radical bonded via a $C_{1-2}$-alkylene group, $R^{22}$=H, NHNH$_2$, NHR$^{18}$, a $C_{1-10}$-alkyl, an aryl or a heteroaryl radical or an aryl or heteroaryl radical bonded via a $C_{1-6}$-alkylene group, preferably H, a $C_{1-6}$-alkyl radical, an aryl radical bonded via a $C_{1-2}$-alkylene group, NHNH$_2$, NHR$^{18}$ or a phenyl radical which is optionally substituted by F, Cl, Br, $C_{1-4}$-alkyl or $C_{1-3}$-alkoxy, particularly preferably NHNH$_2$, NHR$^{18}$ or a phenyl radical which is optionally substituted by F, Cl, Br, $C_{1-4}$-alkyl or $C_{1-3}$-alkoxy, very particularly preferably NHNH$_2$ or NHR$^{18}$, and/or their racemates, enantiomers, diastereomers and/or corresponding bases and/or corresponding salts of physiologically tolerated acids, excluding the racemates of the compounds in which the radicals $R^1$=CH($R^9$)N($R^{10}$)($R^{11}$) and $R^2$=OR$^{12}$ and in each case the radicals $R^3$ to $R^8$ and $R^{12}$=H, the radical $R^9$=phenyl, 2-chlorophenyl, 4-methoxyphenyl, 3-fluorophenyl, 3-chlorophenyl, 3-bromophenyl, 4-bromophenyl, 2-fluorophenyl, 2-bromophenyl, benzo-1,3-dioxole, 4-CH$_3$OCO-phenyl or 2-methoxyphenyl and the radicals $R^{10}$ and $R^{11}$ together=(CH$_2$)$_5$ or, the radicals $R^3$ to $R^8$ and $R^{12}$=H, the radical $R^9$=phenyl, 4-methoxyphenyl, 4-dimethylaminophenyl, 4-hydroxy-2,3-di-tert-butylphenyl, 2,3-dihydrobenzodioxane, 4-nitrophenyl or benzo-1,3-dioxole and the radicals $R^{10}$ and $R^{11}$ together=(CH$_2$)$_2$O(CH$_2$)$_2$ or the radicals $R^3$ to $R^8$ and $R^{12}$=H, the radical $R^9$=4-methoxyphenyl and the radicals $R^{10}$ and $R^{11}$ together=(CH$_2$)$_4$ or the radical $R^3$=CO(OR$^{20}$), the radicals $R^4$ to $R^8$ and $R^{12}$=H, the radical $R^9$=phenyl, 4-methoxyphenyl, 4-methylphenyl, 4-nitrophenyl or p-benzaldehyde, the radicals $R^{10}$ and $R^{11}$ together=(CH$_2$)$_5$ and the radical $R^{20}$=CH$_3$ or the radicals $R^3$ to $R^8$ and $R^{12}$=H, the radical $R^9$=phenyl and the two radicals $R^{10}$ and $R^{11}$ each=CH$_3$, C$_2$H$_5$ or n-C$_3$H$_7$ or the radicals $R^3$ to $R^8$ and $R^{12}$=H, the radical $R^9$=4-methoxyphenyl or benzo-1,3-dioxole and the radicals $R^{10}$ and $R^{11}$ each=CH$_3$ or the radicals $R^3$ to $R^5$, $R^7$, $R^8$, $R^{12}$=H, the radical $R^6$=Br, the radical $R^9$=phenyl and the radicals $R^{10}$ and $R^{11}$ together=(CH$_2$)$_5$ or the radicals $R^3$ to $R^5$, $R^7$, $R^8$, $R^{12}$=H, the radical $R^6$=Br, the radical $R^9$=4-hydroxy-3,5-di-tert-butylphenyl and the radicals $R^{10}$ and $R^{11}$ together (CH$_2$)$_2$O (CH$_2$)$_2$ or the radicals $R^3$ to $R^8$ and $R^{12}$=H, the radical $R^9$=phenyl and the radicals $R^{10}$ and $R^{11}$ each=CH$_3$ as the hydrochloride or the radicals $R^3$ to $R^8$ and $R^{12}$=H, the radical $R^9$=phenyl or 4-methoxyphenyl and the radicals $R^{10}$ and $R^{11}$ together=(CH$_2$)$_5$ as the hydrochloride or the radical $R^3$=CO(OR$^{20}$), the radicals $R^4$ to $R^8$ and $R^{12}$=H, the radical $R^9$=phenyl, the radicals $R^{10}$ and $R^{11}$ together=(CH$_2$)$_5$ and the radical $R^{20}$=CH$_3$ as the hydrochloride or the radicals $R^3$ to $R^8$ and $R^{12}$=H, the radical $R^9$=thiophene and the radicals $R^{10}$ and $R^{11}$ together=(CH$_2$)$_2$O(CH$_2$)$_2$ or the radicals $R^3$ to $R^8$=H, the radical $R^{12}$=CH$_3$, the radical $R^9$=thiophene, 4-methoxyphenyl or 3,4-dimethoxyphenyl and the radicals $R^{10}$ and $R^{11}$ together=(CH$_2$)$_2$O(CH$_2$)$_2$ and the enantiomers of the compound of the general formula I in which $R^1$=CH($R^9$)N($R^{10}$)($R^{11}$) and $R^2$=OR$^{12}$ and the radicals $R^3$ to $R^8$, $R^{12}$=H, $R^9$=phenyl and $R^{10}$ and $R^{11}$ together=(CH$_2$)$_5$ and the racemates of the compounds in which the radicals $R^1$=OR$^{12}$ and $R^2$=CH($R^9$)N($R^{10}$)($R^{11}$) and in each case the radicals $R^3$ to $R^8$ and $R^{12}$=H, the radical $R^9$=phenyl, 2-bromophenyl, 3-bromophenyl or 4-bromophenyl and the radicals $R^{10}$ and $R^{11}$ together=(CH$_2$)$_5$ or $R^3$ to $R^8$ and $R^{12}$=H, the radical $R^9$=phenyl or 2-nitrophenyl and the radicals $R^{10}$ and $R^{11}$ together=(CH$_2$)$_2$O(CH$_2$)$_2$ or $R^3$, $R^4$, $R^6$, $R^8$ and $R^{12}$=H, the radicals $R^5$, $R^7$=CH$_3$, the radical $R^9$=phenyl or 4-methoxyphenyl and the radicals $R^{10}$ and $R^{11}$ together=(CH$_2$)$_5$ or $R^3$ to $R^6$, $R^8$, $R^{12}$=H, the radical $R^7$=CH$_3$, the radical $R^9$=4-methoxyphenyl or phenyl and the radicals $R^{10}$, $R^{11}$ together=(CH$_2$)$_5$ or $R^3$ to $R^8$ and $R^{12}$=H, the radical $R^9$=phenyl, the radical $R^{10}$=CH$_3$ and the radical $R^{11}$=C$_6$H$_{11}$ or the radicals $R^{10}$ and $R^{11}$ each=CH$_3$ or $R^3$ to $R^6$, $R^8$, $R^{12}$=H, the radical $R^7$=CH$_3$, the radical $R^9$=phenyl or 4-methoxyphenyl and the radicals $R^{10}$ and $R^{11}$ together=(CH$_2$)$_2$O(CH$_2$)$_2$ or $R^3$, $R^4$, $R^6$, $R^8$, $R^{12}$=H, the radicals $R^5$ and $R^7$=CH$_3$, the radical $R^9$=4-methoxyphenyl and the radicals $R^{10}$ and $R^{11}$ together=(CH$_2$)$_2$O(CH$_2$)$_2$ or $R^3$ to $R^8$, $R^{12}$=H, the radical $R^9$=phenyl and the radicals $R^{10}$ and $R^{11}$ together=(CH$_2$)$_2$O(CH$_2$)$_2$ as the hydrochloride.

DETAILED DESCRIPTION OF THE PREFERRED EMBODIMENTS

Figure 1:
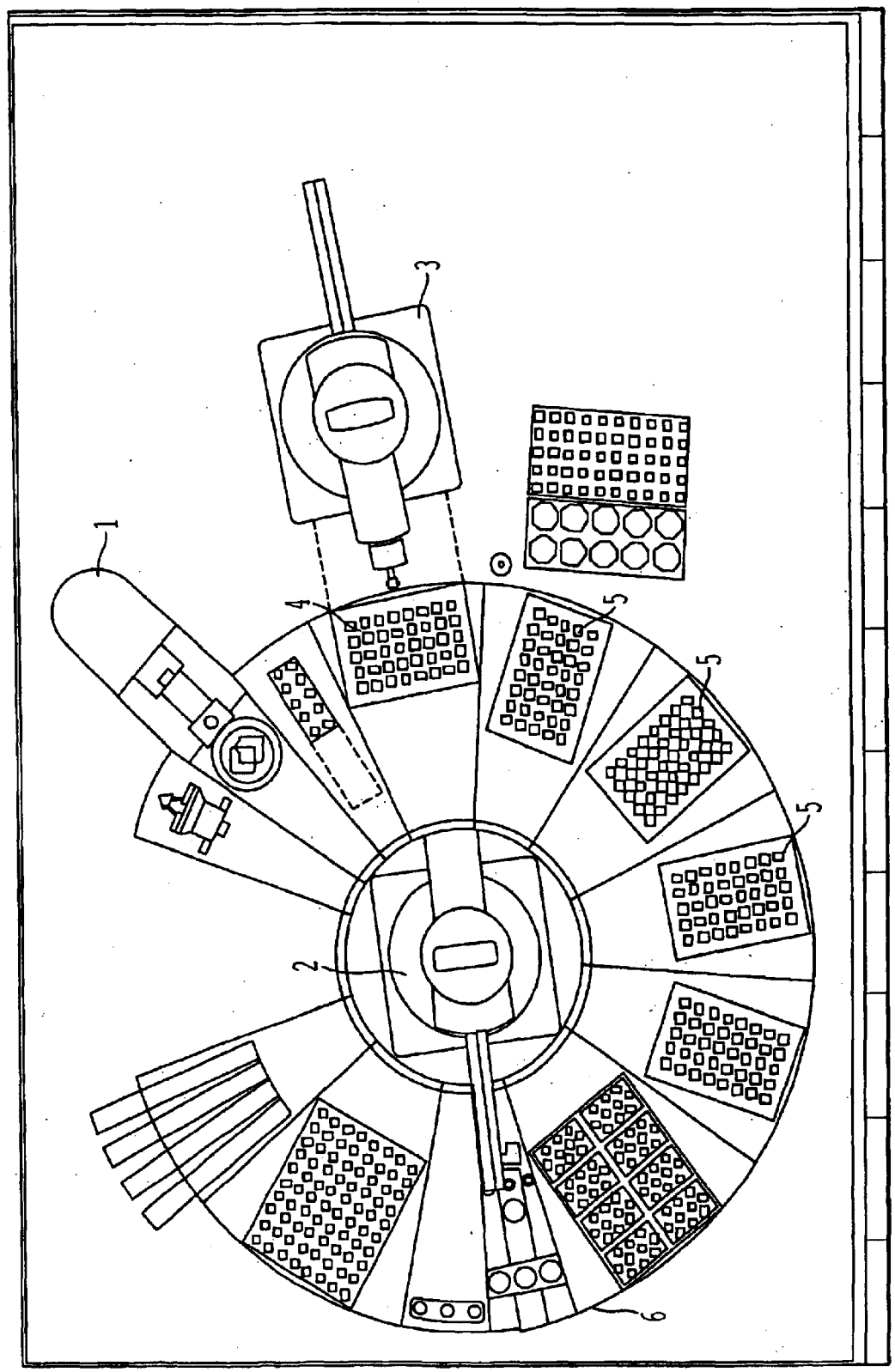
FIG. 1 shows as automatic unit for the synthesis of a Mannich base in the present invention.

Alkyl radicals are preferably understood as hydrocarbon radicals which are at least monosubstituted by halogen, CN, $CF_3$ and/or OH, particularly preferably by F, Cl, Br or OH. If these contain more than one substituent, these substituents can be identical or different. The alkyl radicals can be branched, unbranched or cyclic. The alkyl radicals methyl, ethyl, propyl, 1-methylethyl, butyl, 1-methylpropyl, 2-methylpropyl, 1,1-dimethylpropyl, 1,2-dimethylpropyl, 2,2-dimethylpropyl, hexyl, 1-methylpentyl, heptyl, nonyl or decanyl are particularly preferred.

An aryl radical is preferably understood as phenyl or naphthyl radicals which are at least monosubstituted by an OH, a halogen, preferably F, Br or Cl, a $CF_3$, a CN, a $C_{1-6}$-alkyl, a $C_{1-6}$-alkoxy or a phenyl radical. The unsubstituted or substituted phenyl radicals can also be fused with further rings. The aryl radicals 2-, 3- and 4-bromophenyl, 4-bromo-2-fluorophenyl, 5-bromo-2-fluorophenyl, 3-bromo-4-fluorophenyl, 4-tert-butylphenyl, 2-chloro-4-fluorophenyl, 2-chloro-6-fluorophenyl, 4-cyanophenyl, 2,3-dichlorophenyl, 2,4-dichlorophenyl, 2,6-dichlorophenyl, 3,4-dichlorophenyl, 2,3-dimethoxyphenyl, 3,4-dimethoxyphenyl, 2,4-dimethylphenyl, 2,5-dimethylphenyl, 2-, 3- and 4-fluorophenyl, 2-methoxyphenyl, 2-, 3- and 4-methylphenyl, 3-phenoxyphenyl, 2- and 4-trifluoromethylphenyl or 3,4,5-trimethoxyphenyl are particularly preferred.

A heteroaryl radical is understood as aromatic compounds which have at least one heteroatom, preferably nitrogen and/or oxygen and/or sulfur, particularly preferably nitrogen and/or oxygen, and which can preferably be substituted by a halogen, a CN, a $CF_3$ or an OH radical. The heteroaryl radical is very particularly preferably a substituted or unsubstituted thiophene, pyrrolyl or furfuryl radical.

The following substituted 1- and 2-naphthol Mannich bases are particularly preferred:

6-(dimethylaminophenylmethyl)-5-hydroxy-naphthalene-1-sulfonic acid amide
4-amino-2-(dimethylaminophenylmethyl)-naphthalen-1-ol
4-(dimethylaminophenylmethyl)-3-hydroxy-naphthalene-2-carboxylic acid hydrazide
4-(dimethylaminophenylmethyl)-3-hydroxy-naphthalene-2-carboxylic acid methyl ester
4-(dimethylaminophenylmethyl)-3-hydroxy-naphthalene-2-carboxylic acid
4-(dimethylaminophenylmethyl)-3-hydroxy-naphthalene-2-carboxylic acid phenyl ester
[5-(dimethylaminophenylmethyl)-6-hydroxy-naphthalen-2-yl]-phenylmethanone
3-amino-1-(dimethylaminophenylmethyl)-naphthalen-2-ol
4-(dimethylaminophenylmethyl)-3-hydroxy-naphthalene-2-carboxylic acid (2-methoxy-phenyl)-amide
4-(dimethylaminophenylmethyl)-3-hydroxy-naphthalene-2-carboxylic acid o-tolylamide
4-(dimethylaminophenylmethyl)-3-hydroxy-naphthalene-2-carboxylic acid naphthalen-1-ylamide
4-(dimethylaminophenylmethyl)-3-hydroxy-7-methoxy-naphthalene-2-carboxylic acid
5-(dimethylaminophenylmethyl)-6-hydroxy-naphthalene-2-carboxylic acid
1-(dimethylaminophenylmethyl)-7-methoxy-naphthalen-2-ol
1-(dimethylaminophenylmethyl)-6-methoxy-naphthalen-2-ol
5-(dimethylaminophenylmethyl)-6-hydroxy-naphthalene-1-carboxylic acid
4-(dimethylaminophenylmethyl)-3-hydroxy-7-methoxy-naphthalene-2-carboxylate sodium salt
4-chloro-2-(morpholin-4-yl-o-tolylmethyl)-naphthalen-1-ol
4-chloro-2-(piperidin-1-yl-o-tolylmethyl)-naphthalen-1-ol
4-chloro-2-[(2-chlorophenyl)-piperidin-1-yl-methyl]-naphthalen-1-ol
4-chloro-2-[(2,3-dimethoxyphenyl)-morpholin-4-yl-methyl]-naphthalen-1-ol
5-amino-2-[(2-chlorophenyl)-piperidin-1-yl-methyl]-naphthalen-1-ol
5-amino-2-[(2,3-dimethoxyphenyl)-morpholin-4-yl-methyl]-naphthalen-1-ol
3-hydroxy-4-(piperidin-1-yl-o-tolylmethyl)-naphthalene-2-carboxylic acid hydrazide
7-methoxy-1-(morpholin-4-yl-o-tolylmethyl)-naphthalen-2-ol
1-[(2-chlorophenyl)-piperidin-1-yl-methyl]-7-methoxy-naphthalen-2-ol
1-[(2,3-dimethoxyphenyl)-morpholin-4-yl-methyl]-7-methoxy-naphthalen-2-ol
6-bromo-1-[(2-methoxyphenyl)-morpholin-4-yl-methyl]-naphthalen-2-ol
6-hydroxy-5-[(2-methoxyphenyl)-morpholin-4-yl-methyl]-naphthalene-1-carboxylic acid
7-methoxy-1-[(2-methoxyphenyl)-morpholin-4-yl-methyl]-naphthalen-2-ol
6-methoxy-1-[(2-methoxyphenyl)-morpholin-4-yl-methyl]-naphthalen-2-ol
4-chloro-2-[(2-methoxyphenyl)-piperidin-1-yl-methyl]-naphthalen-1-ol
6-bromo-1-[(2-methoxyphenyl)-piperidin-1-yl-methyl]-naphthalen-2-ol
6-methoxy-1-[(2-methoxyphenyl)-piperidin-1-yl-methyl]-naphthalen-2-ol
7-methoxy-1-[(2-methoxyphenyl)-piperidin-1-yl-methyl]-naphthalen-2-ol
5-chloro-2-[dimethylamino-(2-methoxyphenyl)-methyl]-naphthalen-1-ol
{[1-(4-methoxybenzyloxy)-naphthalen-2-yl]-phenylmethyl}-dimethylamine
{[2-(4-methoxybenzyloxy)-naphthalen-1-yl]-phenylmethyl}-dimethylamine
4-methoxybenzoic acid 1-(dimethylaminophenylmethyl)-naphthalen-2yl ester
2-chlorobenzoic acid 1-(dimethylaminophenylmethyl)-naphthalen-2-yl ester
1-(morpholin-4-yl-phenylmethyl)-naphthalen-2-ol
1-(phenylpiperidin-1-yl-methyl)-naphthalen-2-ol
2-[(4-fluoro-phenyl)-pyrrolidin-1-yl-methyl]-naphthalen-1-ol.

The invention also provides processes for the preparation of substituted 1- and 2-naphthol Mannich bases of the general formula I in which the radical $R^{12}$ represents H and the radicals $R^1$ to $R^{11}$, the radicals $R^{13}$ to $R^{18}$ and the radicals $R^{20}$ to $R^{22}$ have the meaning according to the general formula I, which are characterized in that aromatic aldehyde compounds, heteroaromatic aldehyde compounds and/or aliphatic aldehyde compounds of the general formula II

II in which $R^9$ has the meaning according to the general formula I, are reacted in solution, preferably in an organic solvent, particularly preferably in toluene, in the presence of a base, preferably potassium carbonate or boric acid anhydride, preferably at a temperature of −10° C. to +110° C., with secondary amines of the general formula III

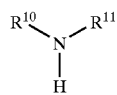

III in which the radicals $R^{10}$ and $R^{11}$ have the meaning according to the general formula I, to give aminal compounds of the general formula IV

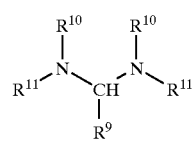

IV and these aminal compounds of the general formula IV are reacted, without further purification, with an acid chloride, preferably with acetyl chloride, in an absolute solvent, preferably in diethyl ether, to give iminium salts of the general formula V

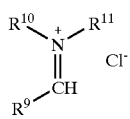

V and these iminium salts of the general formula V are reacted, without further purification and in solution, preferably in acetonitrile, with substituted and/or unsubstituted naphthol compounds of the general formula VI

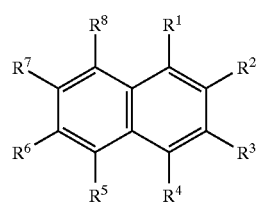

VI wherein $R^1$=H and $R^2$=OH or $R^1$=OH and $R^2$=H and the radicals $R^3$ to $R^8$, $R^{13}$ to $R^{18}$ and $R^{20}$ to $R^{22}$ have the meaning according to the general formula I, and the 1- and 2-naphthol compounds of the general formula I obtained in this way in which the radical $R^{12}$ represents H and the radicals $R^1$ to $R^{11}$, the radicals $R^{13}$ to $R^{18}$ and the radicals $R^{20}$ to $R^{22}$ have the meaning according to the general formula I are purified by extraction and are isolated by conventional methods.

The present invention furthermore also provides processes for the preparation of substituted 1- and 2-naphthol Mannich bases of the general formula I in which the radical $R^{12}$=$COR^{22}$, a $C_{1-10}$-alkyl, an aryl or a heteroaryl radical or an aryl or heteroaryl radical bonded via a $C_{1-6}$-alkylene group and the radicals $R^1$ to $R^{11}$, $R^{13}$ to $R^{18}$ and $R^{20}$ to $R^{22}$ have the meaning according to the general formula I, which are characterized in that aromatic aldehyde compounds, heteroaromatic aldehyde compounds and/or aliphatic aldehyde compounds of the general formula II

II in which $R^9$ has the meaning according to the general formula I, are reacted in solution, preferably in an organic solvent, particularly preferably in toluene, in the presence of a base, preferably potassium carbonate or boric acid anhydride, preferably at a temperature of −10 to +110° C., with secondary amines of the general formula III

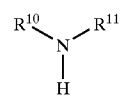

III in which the radicals $R^{10}$ and $R^{11}$ have the meaning according to the general formula I, to give aminal compounds of the general formula IV

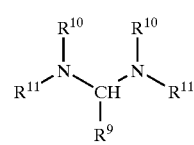

IV and these aminal compounds of the general formula IV are reacted, without further purification, with an acid chloride, preferably with acetyl chloride, in an absolute solvent, preferably in diethyl ether, to give iminium salts of the general formula V

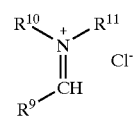

V and these iminium salts of the general formula V are reacted, without further purification and in solution, preferably in acetonitrile, with substituted and/or unsubstituted naphthol compounds of the general formula VI

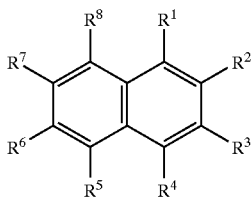

VI wherein $R^1$=H and $R^2$=OH or $R^1$=OH and $R^2$=H and in each case the radicals $R^3$ to $R^8$, $R^{13}$ to $R^{18}$ and $R^{20}$ to $R^{22}$ have the meaning according to the general formula I, and the compounds of the general formula VI obtained in this way, wherein $R^1$=CH($R^9$)N($R^{10}$)($R^{11}$) and $R^2$=OH or $R^1$=OH and $R^2$=CH($R^9$)N($R^{10}$)($R^{11}$) and in each case the radicals $R^3$ to $R^{11}$, $R^{13}$ to $R^{18}$ and $R^{20}$ to $R^{22}$ have the meaning according to the general formula I, are reacted in solution, preferably in dimethylformamide, with compounds of the general formula $XR^{12'}$, wherein X=Cl, Br or I, preferably Cl, and $R^{12'}$ represents $COR^{22}$, a $C_{1-10}$-alkyl, an aryl or a heteroaryl radical or an aryl or heteroaryl radical bonded via a $C_{1-6}$-alkylene group, preferably a $C_{1-6}$-alkyl radical or an aryl radical bonded via a $C_{1-2}$-alkylene group, in the presence of a base, preferably triethylamine or potassium tert-butylate, preferably at a temperature of 10 to 150° C., and the 1- and 2-naphthol Mannich bases of the general formula I obtained in this way, in which the radical $R^{12}$ represents $COR^{22}$, a $C_{1-10}$-alkyl, an aryl or a heteroaryl radical or an aryl or heteroaryl radical bonded via a $C_{1-6}$-alkylene group, preferably a $C_{1-6}$-alkyl radical or an aryl radical bonded via a $C_{1-2}$-alkylene group, and the radicals $R^1$ to $R^{11}$, $R^{13}$ to $R^{18}$ and $R^{20}$ to $R^{22}$ have the meaning according to the general formula I, are purified by filtration, preferably by filtration over a scavenger resin, particularly preferably by filtration over polymer-bonded tris (2-aminoethyl)amine (Novabiochem, Bad Soden) and/or 3-(3-mercaptophenyl)-propane-amidomethylpolystyrene (Argonaut, Muttenz, Switzerland).

The synthesis of the substituted 1- and 2-naphthol Mannich bases according to the invention is preferably carried out on an automatic unit from Zymark according to FIG. 1 and FIG. 2 as described below.

The substituted 1- and 2-naphthol Mannich bases of the general formula I according to the invention can be converted into their salts in a manner known per se to the expert with physiologically tolerated acids, preferably with hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid. The salt formation is preferably carried out in a solvent, particularly preferably in diethyl ether, diisopropyl ether, acetic acid alkyl esters, preferably ethyl acetate, acetone and/or 2-butanone. The salt formation is very particularly preferably carried out with trimethylchlorosilane in methyl ethyl ketone.

The substituted 1- and 2-naphthol Mannich bases of the general formula I according to the invention are toxicologically acceptable and are therefore suitable pharmaceutical active compounds.

The invention therefore also provides medicaments which comprise, as the active compound, at least one substituted 1- and/or 2-naphthol Mannich base of the general formula I and optionally further active compounds and/or auxiliary substances.

The medicament can preferably also comprise a mixture of enantiomers of at least one substituted 1-naphthol Mannich base and/or 2-naphthol Mannich base of the general formula I, the mixture preferably not comprising equimolar amounts of the enantiomers. The relative proportion of one of the enantiomers is particularly preferably 5 to 45 mol %, very particularly preferably 10 to 40 mol %, based on the total mixture of the enantiomers.

The medicaments are preferably employed for treatment of/combating pain and/or inflammatory reactions and/or allergic reactions and/or drug abuse and/or alcohol abuse and/or diarrhoea and/or gastritis and/or ulcers and/or cardiovascular diseases and/or urinary incontinence and/or depression and/or states of shock and/or migraines and/or narcolepsy and/or excess weight and/or asthma and/or glaucoma and/or hyperkinetic syndrome.

The present invention also provides the use of at least one substituted 1- and/or 2-naphthol Mannich base of the general formula I according to the invention for the preparation of a medicament for treatment of/combating pain and/or inflammatory reactions and/or allergic reactions and/or drug abuse and/or alcohol abuse and/or diarrhoea and/or gastritis and/or ulcers and/or cardiovascular diseases and/or urinary incontinence and/or depression and/or states of shock and/or migraines and/or narcolepsy and/or excess weight and/or asthma and/or glaucoma and/or hyperkinetic syndrome.

In addition to at least one substituted 1- and/or 2-naphthol Mannich base of the general formula I, carrier materials, fillers, solvents, diluents, dyestuffs and/or binders are employed for formulating appropriate pharmaceutical formulations. The choice of auxiliary substances depends on whether the medicament is to be administered orally, intravenously, intraperitoneally, intradermally, intramuscularly, intranasally, buccally or locally, for example on infections of the skin, the mucous membranes and the eyes. The formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration.

The substituted 1- and 2-naphthol Mannich bases of the general formula I according to the invention in a depot in dissolved form or in a patch, optionally with the addition of agents which promote penetration through the skin, are suitable formulations for percutaneous administration. The compounds of the general formula I according to the invention can be released from oral or percutaneous formulation forms in a delayed manner.

The amount of active compound to be administered to the patient varies according to the weight of the patient, the mode of administration, the indication and the severity of the disease.

Pharmacological Studies

1.) In vitro Tests

Wide-ranging testing of the 1- and 2-naphthol Mannich bases according to the invention for their activity was carried out by the conventional high throughput screening methods, such as are described in John P. Devlin, High Throughput Screening, 1997, Marcel Dekker Inc. They are introduced herewith as a reference and are therefore part of the disclosure.

The action of the 1- and 2-naphthol Mannich bases according to the invention is determined in particular by the affinity for the N-methyl-D-aspartate (NMDA) receptor family, for α-adrenergic receptors and opioid receptors.

2.) Analgesia Test in the Writhing Test in Mice

The in-depth investigation for analgesic activity was carried out in the phenylquinone-induced writhing in mice (modified by I. C. Hendershot, J. Forsaith, J. Pharmacol. Exp. Ther. 125, 237–240 (1959)). Male NMRI mice weighing 25–30 g were used for this. Groups of 10 animals per substance dose received 0.3 ml/mouse of a 0.02% aqueous solution of phenylquinone (phenylbenzoquinone, Sigma, Deisenhofen; preparation of the solution with the addition of 5% ethanol and storage in a water bath at 45° C.) administered intraperitoneally 10 minutes after intravenous administration of the test substances. The animals were placed individually in observation cages. The number of pain-induced stretching movements (so-called writhing reactions=straightening of the body with stretching of the hind extremities) were counted by means of a push-button counter for 5–20 minutes after the administration of phenylquinone. Animals which received only physiological saline solution were also run as a control.

The substances were tested in the standard dose of 10 mg/kg. The inhibition of the writhing reactions by a substance was calculated according to the following equation:

$$\% \text{ inhibition} = 100 - \left[ \frac{\text{writhing reaction of treated animals}}{\text{writhing reaction of control}} \times 100 \right]$$

The following examples serve to illustrate the invention, but do not limit the general inventive idea.

EXAMPLES

General Synthesis Instructions for the Preparation of Aminal Compounds of the General Formula IV General Synthesis Instructions 1:

1.0 equivalent of the particular aromatic, heteroaromatic or aliphatic aldehyde compound of the general formula II was slowly added dropwise, while stirring at 20° C., to 2.7 equivalents of a 40% solution of the particular secondary amine with the general formula III. The solution was then subsequently stirred at a temperature of 80° C. for a further 30 minutes and then cooled to room temperature, and 0.57 equivalent of potassium carbonate was added. Two phases formed here and were separated from one another, the aqueous phase being extracted three times with 100 ml ethyl acetate each time. The combined organic phases were dried over potassium carbonate and freed from the solvent. The aminal compounds of the general formula IV obtained in this way were then employed in the subsequent reactions without further purification.

General Synthesis Instructions 2:

1.6 equivalents of boric acid anhydride were added to a solution of 1.0 equivalent of the particular aromatic, heteroaromatic or aliphatic aldehyde compound of the general formula II in 80 ml absolute toluene. A solution of 2.4 equivalents of a secondary amine of the general formula III in 85 ml absolute toluene was then added with vigorous stirring. Starting of the reaction could be seen by a significant increase in temperature. The reaction solution was then subsequently stirred at a temperature of 45 to 50° C. for a further two hours. After cooling to room temperature the excess boric acid anhydride was separated off and the filtrate was freed from the solvent. The aminal compounds of the general formula IV obtained in this way were employed in the subsequent reactions without further purification.

General Synthesis Instructions for the Synthesis of Iminium Salts of the General Formula V General Synthesis Instructions 3:

A solution of 1.0 equivalent of acetyl chloride in absolute diethyl ether was slowly added dropwise, while stirring, to 1.0 equivalent of an ice-cooled solution or suspension of the aminal compound of the general formula IV prepared in accordance with general synthesis instructions 1 or 2. The reaction mixture was then subsequently stirred overnight at approx. 20° C. A precipitate was formed here, and was filtered off with suction under nitrogen and then dried under an oil pump vacuum. The iminium salts of the general formula V obtained in this way were employed in the subsequent reactions without further purification.

Figure 2:
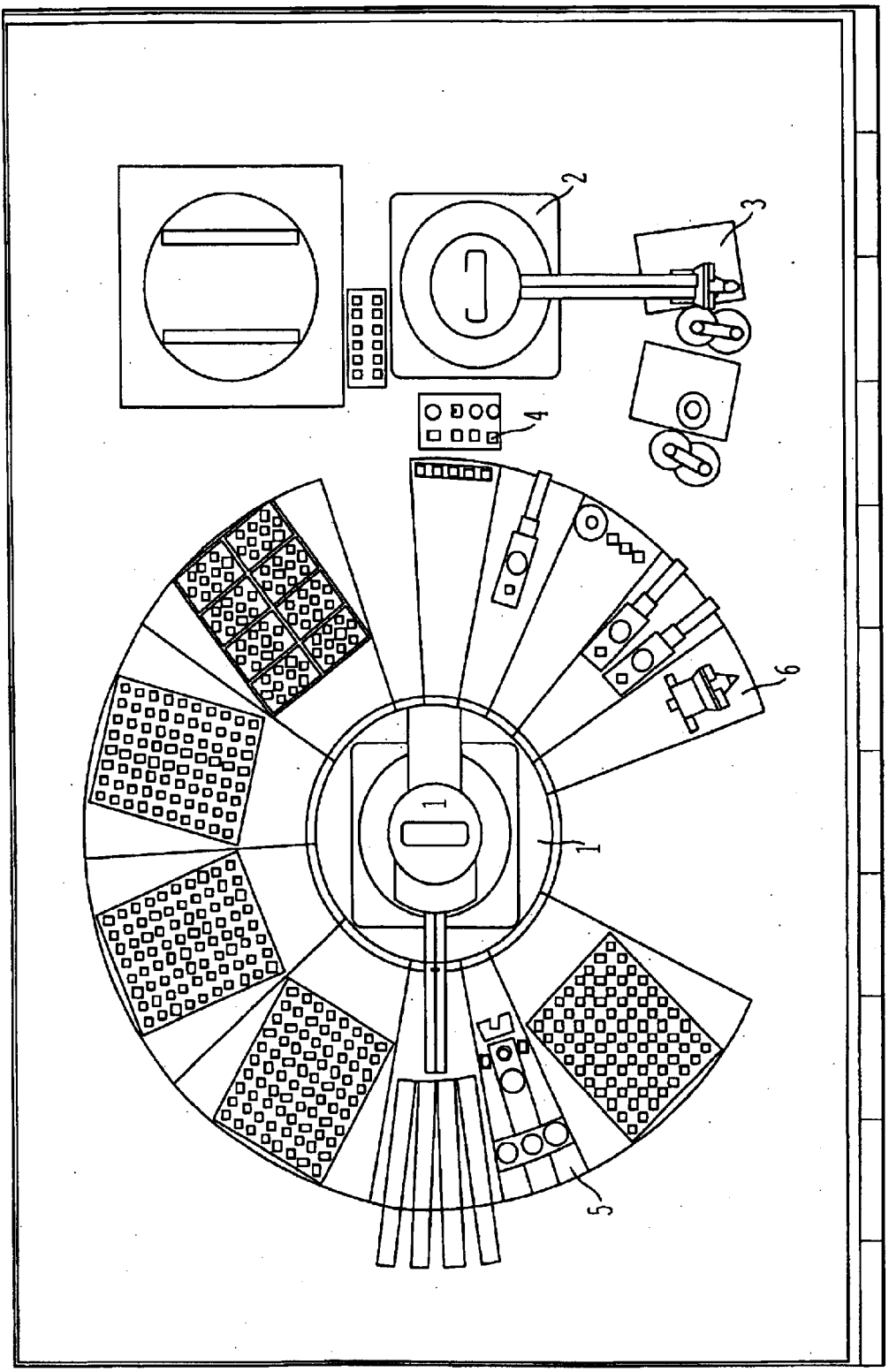
FIG. 2 shows another automatic unit for the synthesis of a Mannich base in the present invention.

General Synthesis Instructions for the Synthesis of 1- and 2-Naphthol Mannich Bases of the General Formula I General Synthesis Instructions 4:

The synthesis of the naphthol Mannich bases according to the invention was carried out on an automatic unit from Zymark according to FIG. 1 and FIG. 2:

FIG. 1 here comprises a capper station (no. 1) for closing the reaction tubes, a robot 1 (no. 2) and a robot 2 (no. 3), robot 1 moving the reaction tubes and the corresponding racks and robot 2 pipetting the reagents into the reaction tubes, a temperature-controllable reactor block (no. 4), stirrer blocks (no. 5) and a filtration station (no. 6), in which the reaction solution is filtered.

FIG. 2 also comprises a robot 1 (no. 1) and a robot 2 (no. 2), both of which move the glass tubes with the synthesis products to the various stations. The stations are, specifically, a vortexer (no. 3) for thorough mixing of the samples and for metering in solutions or solvents, a spin reactor (no. 4) for thorough mixing of samples, a phase detection station (no. 5) for detection of the phase boundary and phase separation, and a station (no. 6) for drying the synthesis products over salt cartridges.

For the synthesis, a round-bottomed tube of glass (diameter 16 mm, length 125 mm) with a screw-thread was provided manually with a stirrer and closed with a screw-cap with a septum on the capper station (no. 1) according to FIG. 1.

The tube was placed by robot 1 (no. 2) in the reactor block (no. 4), which was temperature-controlled at 25° C. Robot 2 (no. 3) pipetted in the following reagents in succession:

1.) 1 ml of a 0.1 M solution of 1- or 2-naphthol or a substituted 1- or 2-naphthol compound of the general formula VI and 14 µl triethylamine in acetonitrile
2.) 1.2 ml of a 0.1 M solution of an iminium salt of the general formula V in acetonitrile The iminium salts were prepared beforehand as described in the following examples. Thereafter, the reaction mixture was stirred at 90° C. in one of the stirrer blocks (no. 5) for 960 min. The reaction solution was then filtered at the filtration station (no. 6). The tube was washed twice here with in each case 1 ml methylene chloride and 200 µl water.

The rack with the tubes was then placed manually on an automatic working-up unit according to FIG. 2. 2 ml water and 2 ml ethyl acetate were added to the reaction mixture there on a vortexer (no. 3).

The mixture was brought to a pH of 1 with 1 ml aqueous 5% hydrochloric acid solution. The components were mixed thoroughly in the spin reactor (no. 4) for ten minutes and a clear phase boundary was formed by the slow decrease in the rotational movement. This phase boundary was detected optically on the phase detection station (no. 5) and the aqueous phase was pipetted off. In the next step 2 ml ethyl acetate were added to this and the mixture was brought to a pH of 11 with 1 ml saturated aqueous sodium bicarbonate solution. The components were mixed again thoroughly in the spin reactor (no. 4) for ten minutes and the organic phase was then pipetted off. In the next step 1.5 ml ethyl acetate was again added to the aqueous phase. The solution was shaken and centrifuged and the organic phase was pipetted off. The combined organic phases were dried over 2.4 g $MgSO_4$ (granulated). The solvent was removed in a vacuum centrifuge.

General Synthesis Instructions for the Synthesis of Alkylated 1- and 2-Naphthol Mannich Bases of the General Formula I General Synthesis Instructions 5:

A solution of 1.0 equivalent of 1- and/or 2-naphthol Mannich base of the general formula I where $R^{12}$=H in absolute N,N-dimethylformamide was treated with 1.0 equivalent of potassium tert-butylate for 15 minutes, 1.0 equivalent of alkylating reagent ($R^{12}$-Hal) was then added and the mixture was subsequently stirred at approx. 20° C. for a further 24 hours. 3.0 equivalents of 3-(3-mercaptophenyl)-propane-amidomethylpolystyrene were then added to this, the components were allowed to react with one another for a further three hours, the PS resin was filtered off and the filtrate was concentrated in vacuo. The residue obtained in this way was taken up in a 1:1 methylene chloride/water mixture, the mixture was stirred for 30 minutes and the phases were separated, the aqueous phase being extracted three times with 20 ml methylene chloride each time. The combined organic phases were dried over magnesium sulfate and freed from the solvent.

General Synthesis Instructions for the Synthesis of Acylated 1- and 2-Naphthol Mannich Bases of the General Formula I General Synthesis Instructions 6:

A solution of 1.0 equivalent of 1- and/or 2-naphthol Mannich base of the general formula I where $R^{12}$=H in absolute N,N-dimethylformamide was treated with 1.0 equivalent of potassium tert-butylate for 15 minutes, 1.0 equivalent of acylating reagent ($R^{12}$-Hal) was then added and the mixture was subsequently stirred at approx. 20° C. for a further 24 hours. 3.0 equivalents of polymer-bonded tris(2-aminoethyl)amine were then added to this, the components were allowed to react with one another for a further three hours, the PS resin was filtered off and the filtrate was concentrated in vacuo. The residue obtained in this way was taken up in a 1:1 methylene chloride/water mixture, the mixture was stirred for 30 minutes and the phases were separated, the aqueous phase being extracted three times with 20 ml methylene chloride each time. The combined organic phases were dried over magnesium sulfate and freed from the solvent.

Synthesis of 1- and 2-Naphthol Mannich Bases of the General Formula I

Example 1

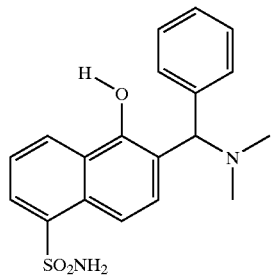

6-(Dimethylaminophenylmethyl)-5-hydroxy-naphthalene-1-sulfonic Acid Amide

1st Stage

Benzylidene-dimethyl-ammonium Chloride

The reaction of 32.0 ml (0.213 mol) dimethylamine solution and 8.0 ml (0.079 mol) benzaldehyde in accordance with general synthesis instructions 1 and subsequent reaction with 4.7 ml (0.079 mol) acetyl chloride in accordance with general synthesis instructions 3 gave 9.5 g (corresponding to 70.7% of the yield calculated by theory) benzylidene-dimethyl-ammonium chloride.

2nd Stage 6-(Dimethylaminophenylmethyl)-5-hydroxy-naphthalene-1-sulfonic Acid Amide The preparation was carried out in accordance with general synthesis instructions 4 from 5-hydroxy-1-naphthalenesulfonamide and benzylidene-dimethyl-ammonium chloride.

The structure was demonstrated by means of ESI-MS: mass calculated 356.45 g/mol, mass found M+H=357.3g/mol.

Example 2

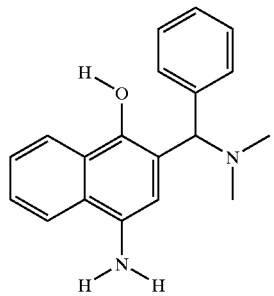

4-Amino-2-(dimethylaminophenylmethyl)-naphthalen-1-ol

The preparation was carried out in accordance with general synthesis instructions 4 from 1-amino-4-naphthol and benzylidene-dimethyl-ammonium chloride, which had been prepared in accordance with example 1.

The structure was demonstrated by means of ESI-MS: mass calculated 292.38 g/mol, mass found M+H=293.8.

Example 3

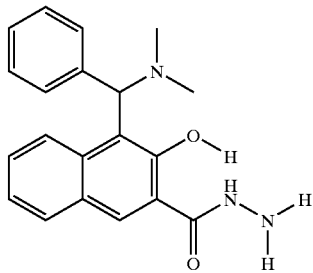

4-(Dimethylaminophenylmethyl)-3-hydroxy-naphthalene-2-carboxylic Acid Hydrazide

The preparation was carried out in accordance with general synthesis instructions 4 from 2-hydroxy-3-naphthoic acid hydrazide and benzylidene-dimethyl-ammonium chloride, which had been prepared in accordance with example 1.

The structure was demonstrated by means of ESI-MS: mass calculated 335.41 g/mol, mass found M+H=336.3

Example 4

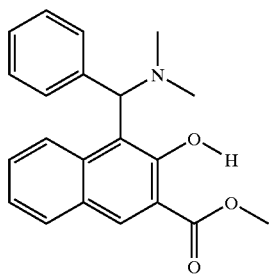

4-(Dimethylaminophenylmethyl)-3-hydroxy-naphthalene-2-carboxylic Acid Methyl Ester The preparation was carried out in accordance with general synthesis instructions 4 from methyl 3-hydroxy-2-naphthoate and benzylidene-dimethyl-ammonium chloride, which had been prepared in accordance with example 1.

The structure was demonstrated by means of ESI-MS: mass calculated 335.41 g/mol, mass found M+H=336.5.

Example 5

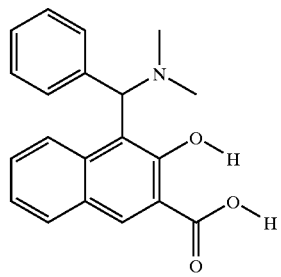

4-(Dimethylaminophenylmethyl)-3-hydroxy-naphthalene-2-carboxylic Acid

The preparation was carried out in accordance with general synthesis instructions 4 from 2-hydroxy-3-naphthoic acid and benzylidene-dimethyl-ammonium chloride, which had been prepared in accordance with example 1.

The structure was demonstrated by means of ESI-MS: mass calculated 321.38 g/mol, mass found M+H=322.2.

Example 6

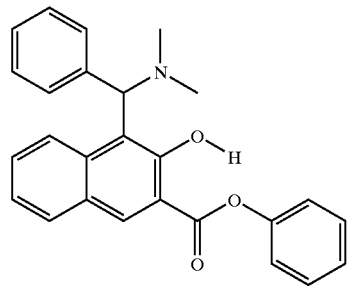

4-(Dimethylaminophenylmethyl)-3-hydroxy-naphthalene-2-carboxylic Acid Phenyl Ester The preparation was carried out in accordance with general synthesis instructions 4 from 2-hydroxy-3-naphthoic acid phenyl ester and benzylidene-dimethyl-ammonium chloride, which had been prepared in accordance with example 1.

The structure was demonstrated by means of ESI-MS: mass calculated 397.48 g/mol, mass found M+H=398.2.

Example 7

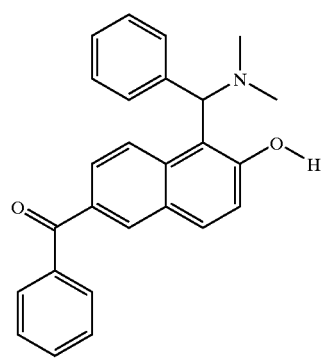

[5-(Dimethylaminophenylmethyl)-6-hydroxy-naphthalen-2-yl]-phenyl-methanone

The preparation was carried out in accordance with general synthesis instructions 4 from 6-benzoyl-2-naphthol and benzylidene-dimethyl-ammonium chloride, which had been prepared in accordance with example 1.

The structure was demonstrated by means of ESI-MS: mass calculated 381.48 g/mol, mass found M+H=382.2.

Example 8

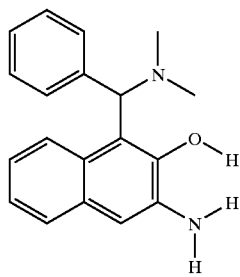

3-Amino-1-(dimethylaminophenylmethyl)-naphthalen-2-ol

The preparation was carried out in accordance with general synthesis instructions 4 from 3-amino-2-naphthol and benzylidene-dimethyl-ammonium chloride, which had been prepared in accordance with example 1.

The structure was demonstrated by means of ESI-MS: mass calculated 292.38 g/mol, mass found M+H=293.3; M+H–NMe$_2$=249.3.

Example 9

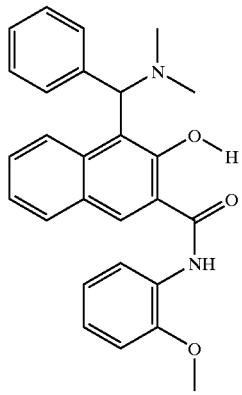

4-(Dimethylaminophenylmethyl)-3-hydroxy-naphthalene-2-carboxylic Acid (2-Methoxy-phenyl)-amide The preparation was carried out in accordance with general synthesis instructions 4 from 3-hydroxy-N-(2-methoxyphenyl)-2-naphthalenecarboxamide and benzylidene-dimethyl-ammonium chloride, which had been prepared in accordance with example 1.

The structure was demonstrated by means of ESI-MS: mass calculated 426.52 g/mol, mass found M+H=427.0.

Example 10

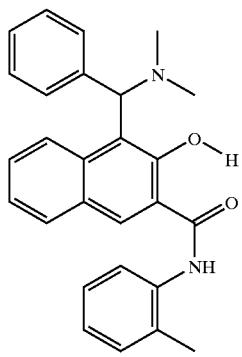

4-(Dimethylaminophenylmethyl)-3-hydroxy-naphthalene-2-carboxylic Acid o-Tolylamide The preparation was carried out in accordance with general synthesis instructions 4 from 3-hydroxy-N-(o-tolyl)-2-naphthalenecarboxamide and benzylidene-dimethyl-ammonium chloride, which had been prepared in accordance with example 1.

The structure was demonstrated by means of ESI-MS: mass calculated 410.52 g/mol, mass found M+H=412.0.

Example 11

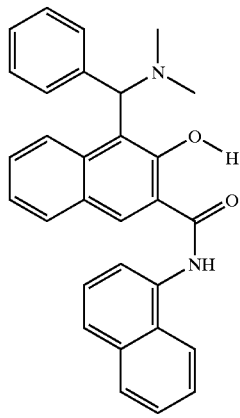

4-(Dimethylaminophenylmethyl)-3-hydroxy-naphthlene-2-carboxylic Acid Naphthalen-1-ylamide The preparation was carried out in accordance with general synthesis instructions 4 from 3-hydroxy-N-(naphthyl)-2-naphthalenecarboxamide and benzylidene-dimethyl-ammonium chloride, which had been prepared in accordance with example 1.

The structure was demonstrated by means of ESI-MS: mass calculated 446.55 g/mol, mass found M+H=447.8.

Example 12

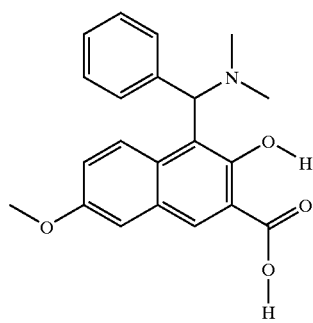

4-(Dimethylaminophenylmethyl)-3-hydroxy-7-methoxy-naphthalene-2-carboxylic Acid

The preparation was carried out in accordance with general synthesis instructions 4 from 3-hydroxy-7-methoxy-2-naphthoic acid and benzylidene-dimethyl-ammonium chloride, which had been prepared in accordance with example 1.

The structure was demonstrated by means of ESI-MS: mass calculated 351.41 g/mol, mass found M+H=352.3.

Example 13

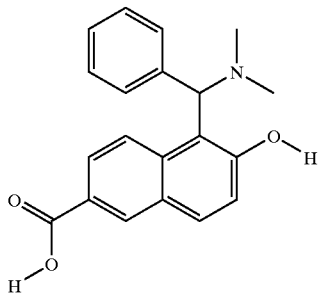

5-(Dimethylaminophenylmethyl)-6-hydroxy-naphthalene-2-carboxylic Acid

The preparation was carried out in accordance with general synthesis instructions 4 from 6-hydroxy-2-naphthoic acid and benzylidene-dimethyl-ammonium chloride, which had been prepared in accordance with example 1.

The structure was demonstrated by means of ESI-MS: mass calculated 321.38 g/mol, mass found M+H=322.1.

Example 14

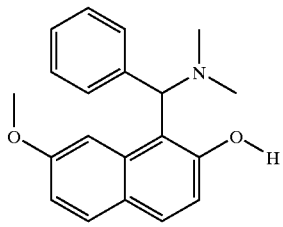

1-(Dimethylaminophenylmethyl)-7-methoxynaphthalen-2-ol

The preparation was carried out in accordance with general synthesis instructions 4 from 7-methoxy-2-naphthol and benzylidene-dimethyl-ammonium chloride, which had been prepared in accordance with example 1.

The structure was demonstrated by means of ESI-MS: mass calculated 307.36 g/mol, mass found M+H=308.4.

Example 15

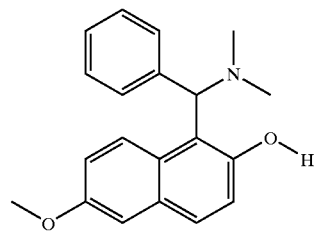

1-(Dimethylaminophenylmethyl)-6-methoxynaphthalen-2-ol

The preparation was carried out in accordance with general synthesis instructions 4 from 6-methoxy-2-naphthol and benzylidene-dimethyl-ammonium chloride, which had been prepared in accordance with example 1.

The structure was demonstrated by means of ESI-MS: mass calculated 307.4 g/mol, mass found M+H=308.3.

Example 16

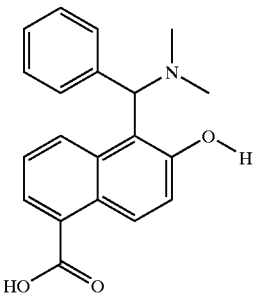

5-(Dimethylaminophenylmethyl)-6-hydroxynaphthalene-1-carboxylic Acid

The preparation was carried out in accordance with general synthesis instructions 4 from 6-hydroxy-1-naphthoic acid and benzylidene-dimethyl-ammonium chloride, which had been prepared in accordance with example 1.

The structure was demonstrated by means of ESI-MS: mass calculated 321.38 g/mol, mass found M+H=322.2.

Example 17

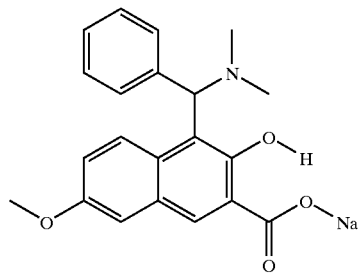

4-(Dimethylaminophenylmethyl)-3-hydroxy-7-methoxynaphthalene-carboxylate Sodium Salt The preparation was carried out in accordance with general synthesis instructions 4 from the sodium salt of 3-hydroxy-7-methoxy-2-naphthoic acid and benzylidene-dimethyl-ammonium chloride, which had been prepared in accordance with example 1.

The structure was demonstrated by means of ESI-MS: mass calculated 373.39 g/mol, mass found M+H−Na=352.0.

Example 18

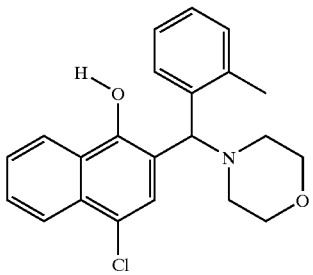

4-Chloro-2-(morpholin-4-yl-o-tolylmethyl)-naphthalen-1-ol

1st Stage 4-(2-Methyl-benzylidene)-morpholin-4-ium Chloride

The reaction of 8.5 g (0.100 mol) morpholine and 7.0 g (0.050 mol) 2-methoxybenzaldehyde in accordance with general synthesis instructions 2 and subsequent reaction with 3.9 g (0.050 mol) acetyl chloride in accordance with general synthesis instructions 3 gave 7.1 g (corresponding to 58% of the yield calculated by theory) 4-(2-methyl-benzylidene)-morpholin-4-ium chloride.

2nd Stage

4-Chloro-2-(morpholin-4-yl-o-tolylmethyl)-naphthalen-1-ol

The preparation was carried out in accordance with general synthesis instructions 4 from 4-chloro-1-naphthol and 4-(2-methyl-benzylidene)-morpholin-4-ium chloride.

The structure was demonstrated by means of ESI-MS: mass calculated 367.88 g/mol, mass found M+H=368.1.

Example 19

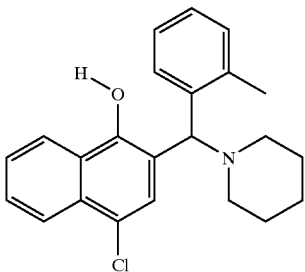

4-Chloro-2-(piperidin-1-yl-o-tolylmethyl)-naphthalen-1-ol

1st Stage 1-(2-Methyl-benzylidene)-piperidinium Chloride

The reaction of 9.5 ml (0.096 mol) piperidine and 4.7 ml (0.040 mol) 2-methylbenzaldehyde in accordance with general synthesis instructions 2 and subsequent reaction with 2.4 ml (0.040 mol) acetyl chloride in accordance with general synthesis instructions 3 gave 5.8 g (corresponding to 65% of the yield calculated by theory) 1-(2-methyl-benzylidene)-piperidinium chloride.

2nd Stage

4-Chloro-2-(piperidin-1-yl-o-tolylmethyl)-naphthalen-1-ol

The preparation was carried out in accordance with general synthesis instructions 4 from 1-(2-methyl-benzylidene)-piperidinium chloride and 4-chloro-1-naphthol.

The structure was demonstrated by means of ESI-MS: mass calculated 365.91 g/mol, mass found M+H=366.2.

Example 20

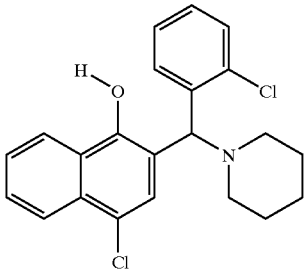

4-Chloro-2-[(2-chlorophenyl)-piperidin-1-yl-methyl]-naphthalen-1-ol

1st Stage 1-(2-Chloro-benzylidene)-piperidinium Chloride

The reaction of 8.5 g (0.100 mol) piperidine and 7.0 g (0.050 mol) 2-chlorobenzaldehyde in accordance with general synthesis instructions 2 and subsequent reaction with 3.9 g (0.050 mol) acetyl chloride in accordance with general synthesis instructions 3 gave 7.1 g (corresponding to 58% of the yield calculated by theory) 1-(2-methyl-benzylidene)-piperidinium chloride.

2nd Stage

4-Chloro-2-[(2-chlorophenyl)-piperidin-1-yl-methyl]-naphthalen-1-ol

The preparation was carried out in accordance with general synthesis instructions 4 from 1-(2-chloro-benzylidene)-piperidinium chloride and 4-chloro-1-naphthol.

The structure was demonstrated by means of ESI-MS: mass calculated 386.32 g/mol, mass found M+H=386.1.

Example 21

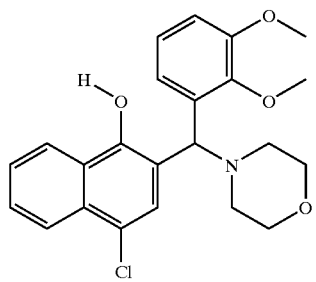

4-Chloro-2-[(2,3-dimethoxyphenyl)-morpholin-4-yl-methyl]-naphthalen-1-ol

1st Stage 4-(2,3-Dimethoxy-benzylidene)-morpholin-4-ium Chloride

The reaction of 7.3 ml (0.084 mol) morpholine and 5.8 g (0.035 mol) 2,3-dimethoxybenzaldehyde in accordance with general synthesis instructions 2 and subsequent reaction with 2.1 ml (0.035 mol) acetyl chloride in accordance with general synthesis instructions 3 gave 5.6 g (corresponding to 59% of the yield calculated by theory) 4-(2,3-dimethoxy-benzylidene)-morpholin-4-ium chloride.

2nd Stage

4-Chloro-2-[(2,3-dimethoxyphenyl)-morpholin-4-yl-methyl]-naphthalen-1-ol

The preparation was carried out in accordance with general synthesis instructions 4 from 4-(2,3-dimethoxy-benzylidene)-morpholin-4-ium chloride and 4-chloro-1-naphthol.

The structure was demonstrated by means of ESI-MS: mass calculated 413.91 g/mol, mass found M+H=414.0.

Example 22

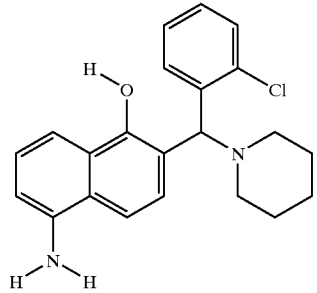

5-Amino-2-[(2-chlorophenyl)-piperidin-1-yl-methyl]-naphthalen-1-ol

The preparation was carried out in accordance with general synthesis instructions 4 from 5-amino-1-naphthol and 1-(2-chloro-benzylidene)-piperidinium chloride, which had been prepared in accordance with example 20.

The structure was demonstrated by means of ESI-MS: mass calculated 366.89 g/mol, mass found M+H=367.4.

Example 23

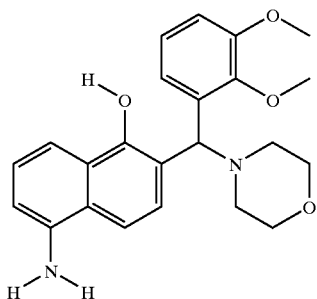

5-Amino-2-[(2,3-dimethoxyphenyl)-morpholin-4-yl-methyl]-naphthalen-1-ol

The preparation was carried out in accordance with general synthesis instructions 4 from 5-amino-1-naphthol and 4-(2,3-dimethoxy-benzylidene)-morpholin-4-ium chloride, which had been prepared in accordance with example 21.

The structure was demonstrated by means of ESI-MS: mass calculated 394.47 g/mol, mass found M+H=395.1.

Example 24

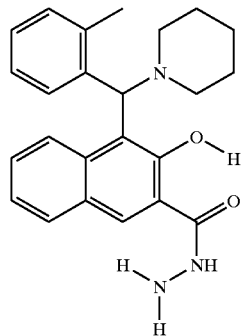

3-Hydroxy-4-(piperidin-1-yl-o-tolylmethyl)-naphthalene-2-carboxylic Acid Hydrazide 1st Stage 1-(2-Methyl-benzylidene)-piperidinium Chloride The reaction of 9.5 ml (0.096 mol) piperidine and 4.7 ml (0.040 mol) 2-methylbenzaldehyde in accordance with general synthesis instructions 2 and subsequent reaction with 2.4 ml (0.040 mol) acetyl chloride in accordance with general synthesis instructions 3 gave 5.8 g (corresponding to 65% of the yield calculated by theory) 1-(2-methyl-benzylidene)-piperidinium chloride.

2nd Stage

3-Hydroxy-4-(piperidin-1-yl-o-tolylmethyl)-naphthalene-2-carboxylic Acid Hydrazide The preparation was carried out in accordance with general synthesis instructions 4 from 1-(2-methyl-benzylidene)-piperidinium chloride and 2-hydroxy-3-naphthoic acid hydrazide.

The structure was demonstrated by means of ESI-MS: mass calculated 389.5 g/mol, mass found M+H=388.5.

Example 25

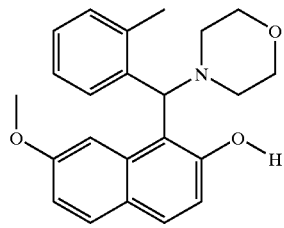

7-Methoxy-1-(morpholin-4-yl-o-tolylmethyl)-naphthalen-2-ol

The preparation was carried out in accordance with general synthesis instructions 4 from 7-methoxy-2-naphthol and 4-(2-methyl-benzylidene)-morpholin-4-ium chloride, which had been prepared in accordance with example 18.

The structure was demonstrated by means of ESI-MS: mass calculated 389.41 g/mol, mass found M+H=389.5.

Example 26

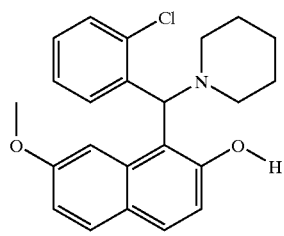

1-[(2-Chlorophenyl)-piperidin-1-yl-methyl)-7-methoxy-naphthalen-2-ol

The preparation was carried out in accordance with general synthesis instructions 4 from 7-methoxy-2-naphthol and 1-(2-chloro-benzylidene)-piperidinium chloride, which had been prepared in accordance with example 20.

The structure was demonstrated by means of ESI-MS: mass calculated 381.91 g/mol, mass found M+H=382.2.

Example 27

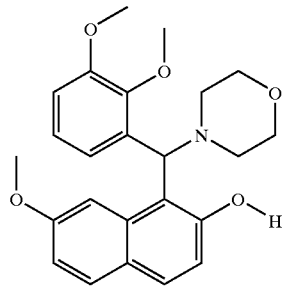

1-[(2,3-Dimethoxyphenyl)-morpholin-4-yl-methyl]-7-methoxy-naphthalen-2-ol

The preparation was carried out in accordance with general synthesis instructions 4 from 7-methoxy-2-naphthol and 4-(2,3-dimethoxy-benzylidene)-morpholin-4-ium chloride, which had been prepared in accordance with example 21.

The structure was demonstrated by means of ESI-MS: mass calculated 409.49 g/mol, mass found M+H=409.9.

Example 28

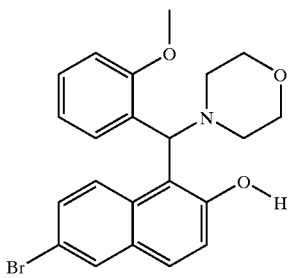

6-Bromo-1-[(2-methoxyphenyl)-morpholin-4-yl-methyl]-naphthalen-2-ol

1st Stage 4-(2-Methoxy-benzylidene)-morpholin-4-ium Chloride

The reaction of 18.8 ml (0.216 mol) morpholine and 12.4 g (0.09 mol) 2-methoxybenzaldehyde in accordance with general synthesis instructions 2 and subsequent reaction with 5.3 ml (0.110 mol) acetyl chloride in accordance with general synthesis instructions 3 gave 7.61 g (corresponding to 38% of the yield calculated by theory) 4-(2-methoxy-benzylidene)-morpholin-4-ium chloride.

2nd Stage

6-Bromo-1-[(2-methoxyphenyl)-morpholin-4-yl-methyl]-naphthalen-2-ol

The preparation was carried out in accordance with general synthesis instructions 4 from 4-(2-methoxy-benzylidene)-morpholin-4-ium chloride and 6-bromo-2-naphthol.

The structure was demonstrated by means of ESI-MS: mass calculated 428.33 g/mol, mass found M+H=428.1/430.0.

Example 29

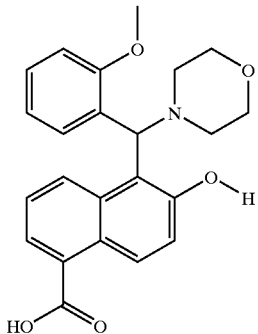

6-Hydroxy-5-[(2-methoxyphenyl)-morpholin-4-yl-methyl]-naphthalene-1-carboxylic Acid The preparation was carried out in accordance with general synthesis instructions 4 from 6-hydroxy-1-naphthoic acid and 4-(2-methoxy-benzylidene)-morpholin-4-ium chloride, which had been prepared in accordance with example 28.

The structure was demonstrated by means of ESI-MS: mass calculated 393.44 g/mol, mass found M+H=394.1.

Example 30

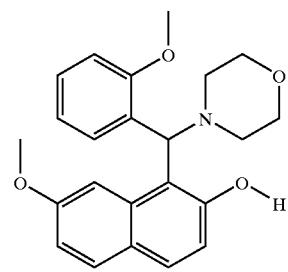

7-Methoxy-1-[(2-methoxyphenyl)-morpholin-4-yl-methyl]-naphthalen-2-ol

The preparation was carried out in accordance with general synthesis instructions 4 from 7-methoxy-2-naphthol and 4-(2-methoxy-benzylidene)-morpholin-4-ium chloride, which had been prepared in accordance with example 28.

The structure was demonstrated by means of ESI-MS: mass calculated 379.46 g/mol, mass found M+H=380.2.

Example 31

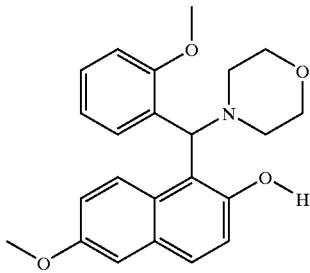

6-Methoxy-1-[(2-methoxyphenyl)-morpholin-4-yl-methyl]-naphthalen-2-ol

The preparation was carried out in accordance with general synthesis instructions 4 from 6-methoxy-2-naphthol and 4-(2-methoxy-benzylidene)-morpholin-4-ium chloride, which had been prepared in accordance with example 28.

The structure was demonstrated by means of ESI-MS: mass calculated 379.46 g/mol, mass found M+H=380.1.

Example 32

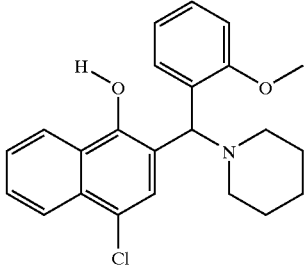

4-Chloro-2-[(2-methoxyphenyl)-piperidin-1-yl-methyl]-naphthalen-1-ol

1st Stage 1-(2-Methoxy-benzylidene)-piperidinium Chloride

The reaction of 18.4 g (0.216 mol) piperidine and 25.9 g (0.090 mol) 2-methoxybenzaldehyde in accordance with general synthesis instructions 2 and subsequent reaction with 5.3 ml (0.11 mol) acetyl chloride in accordance with general synthesis instructions 3 gave 13.4 g (corresponding to 62% of the yield calculated by theory) 1-(2-methoxy-benzylidene)-piperidinium chloride.

2nd Stage

4-Chloro-2-[(2-methoxyphenyl)-piperidin-1-yl-methyl]-naphthalen-1-ol

The preparation was carried out in accordance with general synthesis instructions 4 from 1-(2-methoxy-benzylidene)-piperidinium chloride and 4-chloro-1-naphthol.

The structure was demonstrated by means of ESI-MS: mass calculated 381.91 g/mol, mass found M+H–piperidine=297.2.

Example 33

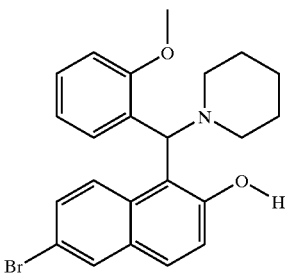

6-Bromo-1-[(2-methoxyphenyl)-piperidin-1-yl-methyl]-naphthalen-2-ol

The preparation was carried out in accordance with general synthesis instructions 4 from 6-bromo-2-naphthol and 1-(2-methoxy-benzylidene)-piperidinium chloride, which had been prepared in accordance with example 32.

The structure was demonstrated by means of ESI-MS: mass calculated 426.36 g/mol, mass found M+H=426.1/428.2.

Example 34

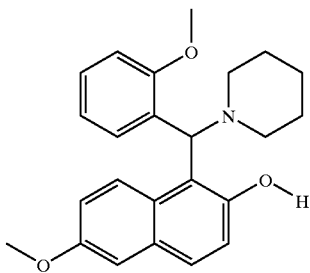

6-Methoxy-1-[(2-methoxyphenyl)-piperidin-1-yl-methyl]-naphthalen-2-ol

The preparation was carried out in accordance with general synthesis instructions 4 from 6-methoxy-2-naphthol and 1-(2-methoxy-benzylidene)-piperidinium chloride, which had been prepared in accordance with example 32.

The structure was demonstrated by means of ESI-MS: mass calculated 377.49 g/mol, mass found M+H=378.2.

Example 35

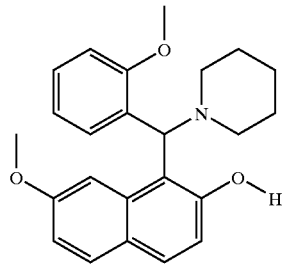

7-Methoxy-1-[(2-methoxyphenyl)-piperidin-1-yl-methyl]-naphthalen-2-ol

The preparation was carried out in accordance with general synthesis instructions 4 from 7-methoxy-2-naphthol and 1-(2-methoxy-benzylidene)-piperidinium chloride, which had been prepared in accordance with example 32.

The structure was demonstrated by means of ESI-MS: mass calculated 377.49 g/mol, mass found M+H=378.2.

Example 36

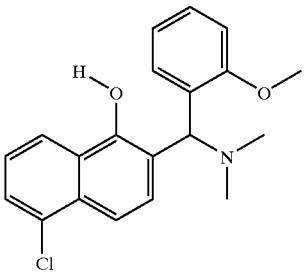

5-Chloro-2-[dimethylamino-(2-methoxyphenyl)-methyl]-naphthalen-1-ol

1st Stage (2-Methoxy-benzylidene)-dimethyl-ammonium Chloride

The reaction of 17.0 ml (0.135 mol) dimethylamine solution and 6.8 ml (0.050 mol) 2-methoxybenzaldehyde in accordance with general synthesis instructions 1 and subsequent reaction with 3.0 ml (0.050 mol) acetyl chloride in accordance with general synthesis instructions 3 gave 4.8 g (corresponding to 48% of the yield calculated by theory) (2-methoxy-benzylidene)-dimethyl-ammonium chloride.

2nd Stage

5-Chloro-2-[dimethylamino-(2-methoxyphenyl)-methyl]-naphthalen-1-ol

The preparation was carried out in accordance with general synthesis instructions 4 from (2-methoxy-benzylidene)-dimethyl-ammonium chloride and 5-chloro-1-naphthol.

The structure was demonstrated by means of ESI-MS: mass calculated 341.84 g/mol, mass found M+H–NMe$_2$=297.2.

Example 37

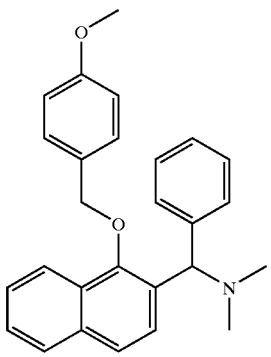

{[1-(4-Methoxy-benzyloxy)-naphthalen-2-yl]-phenylmethyl}-dimethylamine

The preparation was carried out in accordance with general synthesis instructions 4 and 5 from 1-naphthol and benzylidene-dimethyl-ammonium chloride and 4-methoxybenzyl chloride.

The structure was demonstrated by means of $^{13}$C-NMR: δ=159.59; 151.92; 143.30; 134.03; 132.03; 129.22 ($C_q$); 129.76; 128.38; 128.07; 127.99; 126.87; 125.84; 125.74; 124.61; 122.40; 114.10 ($C_t$) 75.85 ($C_s$); 69.46; 55.38; 44.82 ($C_p$).

Example 38

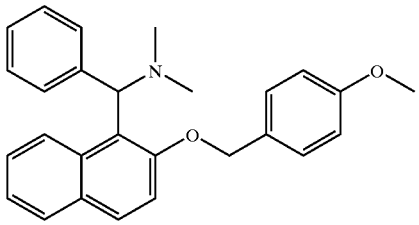

{[2-(4-Methoxybenzyloxy)-naphthalen-1-yl]-phenylmethyl}-dimethylamine

The preparation was carried out in accordance with general synthesis instructions 4 and 5 from 2-naphthol, benzylidene-dimethyl-ammonium chloride and 4-methoxybenzyl chloride. The structure was demonstrated by means of ESI-MS: mass calculated 397.52 g/mol, mass found M+H=398.0.

Example 39

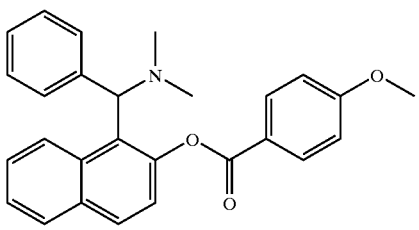

4-Methoxybenzoic Acid 1-(Dimethylaminophenylmethyl)-naphthalen-2-yl Ester

The preparation was carried out in accordance with general synthesis instructions 4 and 6 from 2-naphthol, benzylidene-dimethyl-ammonium chloride and 4-methoxybenzoyl chloride. The structure was demonstrated by means of ESI-MS: mass calculated 411.51 g/mol, mass found M+H=412.0.

Example 40

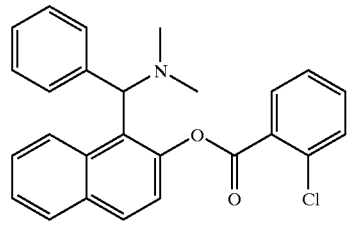

2-Chlorobenzoic Acid 1-(Dimethylaminophenylmethyl)-naphthalen-2-yl Ester

The preparation was carried out in accordance with general synthesis instructions 4 and 6 from 2-naphthol, benzylidene-dimethyl-ammonium chloride and 2-chlorobenzoyl chloride.

The structure was demonstrated by means of ESI-MS: mass calculated 415.92 g/mol, mass found M+H=416.0.

Example 41

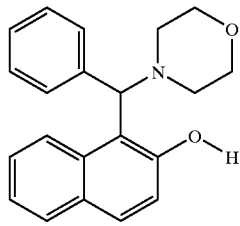

1-(Morpholin-4-yl-phenylmethyl]-naphthalen-2-ol

1st Stage

4-Benzylidene-morpholin-4-ium Chloride

The reaction of 17.9 ml (0.200 mol) morpholine and 10.1 ml (0.100 mol) benzaldehyde in accordance with general synthesis instructions 2 and subsequent reaction with 6.0 ml (0.100 mol) acetyl chloride in accordance with general synthesis instructions 3 gave 10.1 g (corresponding to 48% of the yield calculated by theory) 4-benzylidene-morpholin-4-ium chloride.

2nd Stage 1-(Morpholin-4-yl-phenyl-methyl]-naphthalen-2-ol

The preparation was carried out in accordance with general synthesis instructions 4 from 4-benzylidene-morpholin-4-ium chloride and 2-naphthol.

The structure was demonstrated by means of ESI-MS: mass calculated 319.41 g/mol, mass found M+H=320.1 g/mol.

Example 42

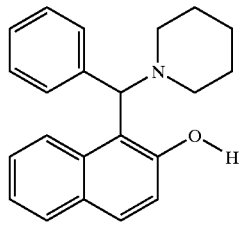

1-(Phenylpiperidin-1-yl-methyl)-naphthalen-2-ol

1st Stage

1-Benzylidene-piperidinium Chloride

The reaction of 19.8 ml (0.200 mol) piperidine and 10.1 ml (0.100 mol) benzaldehyde in accordance with general synthesis instructions 2 and subsequent reaction with 6.0 ml (0.160 mol) acetyl chloride in accordance with general synthesis instructions 3 gave 11.7 g (corresponding to 56% of the yield calculated by theory) 1-benzylidene-piperidinium chloride.

2nd Stage 1-(Phenylpiperidin-1-yl-methyl)-naphthalen-2-ol

The preparation was carried out in accordance with general synthesis instructions 4 from 1-benzylidene-piperidinium chloride and 2-naphthol.

The structure was demonstrated by means of ESI-MS: mass calculated 317.43 g/mol, mass found M+H=318.3 g/mol.

Example 43

2-[(4-Fluoro-phenyl)-pyrrolidin-1-yl-methyl]-naphthalen-1-ol

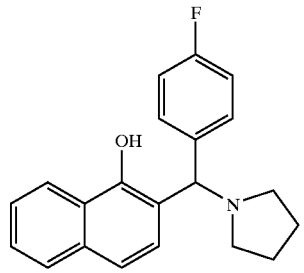

The preparation was carried out in accordance with general synthesis instructions 4 from 1-naphthol and (4-fluoro-benzylidene)-pyrrolidinium chloride, which had been prepared in accordance with example 41 from 4-fluorobenzaldehyde and pyrrolidine.

The structure was demonstrated by means of ESI-MS: mass calculated 321.4 g/mol, mass found M+H=322.1 g/mol, M-pyrrolidine 251.3 g/mol.

Pharmacological Studies

1.) In vitro Tests

The 1- and 2-naphthol Mannich bases according to the invention were tested for their activity as described above.

2.) Analgesia Test in the Writhing Test in Mice

The in-depth investigation for analgesic activity was carried out in the phenylquinone-induced writhing in mice as described above.

The compounds according to the invention investigated showed an analgesic action.

The results of selected writhing investigations are summarized in the following table 1.

TABLE 1

Analgesia test in the writhing test in mice

| Example no. | Inhibition of the writhing reaction in % |
|---|---|
| 37 | 40 |
| 38 | 81 |
| 39 | 21 |
| 40 | 48 |
| 41 | 30 |
| 42 | 92 |

What is claimed is:

1. A substituted 1- and 2-naphthol Mannich base of formula I

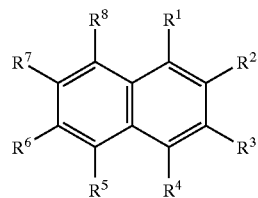

wherein
$R^1$=CH($R^9$)N($R^{10}$)($R^{11}$) and $R^2$=OR$^{12}$ or
$R^1$=OR$^{12}$ and $R^2$=CH($R^9$)N($R^{10}$)($R^{11}$),
and in each case the radicals
$R^3$ to $R^8$ are identical or different and=H, F, Cl, Br, $CF_3$, CN, $NO_2$, $SO_2NH_2$, $SO_2NHR^{13}$, $NHR^{13}$, $SR^{15}$, $OR^{16}$, CO(OR$^{20}$), $CH_2CO(OR^{21})$, CO($R^{22}$), a $C_{1-10}$-alkyl, an aryl radical or an aryl radical bonded via a $C_{1-6}$-alkylene group,
$R^9$ denotes an aryl radical or an alkyl radical without an acid proton in the α-position,
$R^{10}$ and $R^{11}$ together are $(CH_2)_n$, wherein n is 4 or 5,
$R^{12}$=H, COR$^{22}$, a $C_{1-10}$-alkyl, an aryl radical or an aryl radical bonded via a $C_{1-6}$-alkylene group,
$R^{13}$=H, COR$^{14}$, a $C_{1-10}$-alkyl, an aryl radical or an aryl bonded via a $C_{1-6}$-alkylene group,
$R^{14}$=H, a $C_{1-10}$-alkyl, an aryl radical or an aryl bonded via a $C_{1-6}$-alkylene group,
$R^{15}$=H, a $C_{1-10}$-alkyl, an aryl radical or an aryl bonded via a $C_{1-6}$-alkylene group,
$R^{16}$=H, CO($R^{17}$), a $C_{1-10}$-alkyl, an aryl radical or an aryl bonded via a $C_{1-6}$-alkylene group,
$R^{17}$=H, a $C_{1-10}$-alkyl, an aryl radical or an aryl bonded via a $C_{1-6}$-alkylene group,
$R^{18}$=H, a $C_{1-10}$-alkyl, an aryl radical or an aryl bonded via a $C_{1-6}$-alkylene group,
$R^{20}$=H, a $C_{1-10}$-alkyl, an aryl radical or an aryl bonded via a $C_{1-6}$-alkylene group,
$R^{21}$=H, a $C_{1-10}$-alkyl, an aryl radical or an aryl bonded via a $C_{1-6}$-alkylene group,
$R^{22}$=H, $NHNH_2$, NHR$^{18}$, a $C_{1-10}$-alkyl, an aryl radical or an aryl bonded via a $C_{1-6}$-alkylene group,
or a racemate, enantiomer, diastereomer, a corresponding base of a physiologically tolerated acid or a corresponding salt of physiologically tolerated acid thereof,
excluding
the racemates of the compounds in which the radical $R^1$=CH($R^9$)N($R^{10}$)($R^{11}$) and $R^2$=OR$^{12}$ and in each case the radicals $R^3$ to $R^8$ and $R^{12}$=H, the radical $R^9$=phenyl, 2-chlorophenyl, 4-methoxyphenyl, 3-fluorophenyl, 3-chlorophenyl, 3-bromophenyl, 4-bromophenyl, 2-fluorophenyl, 2-bromophenyl, benzo-1,3-dioxole, 4-$CH_3$OCO-phenyl or 2-methoxyphenyl and the radicals $R^{10}$ and $R^{11}$ together=$(CH_2)_5$ or
the radicals $R^3$ to $R^8$ and $R^{12}$=H, the radical $R^9$=4-methoxyphenyl and the radicals $R^{10}$ and $R^{11}$ together=$(CH_2)_4$ or
the radical $R^3$=CO(OR$^{20}$), the radicals $R^4$ to $R^8$ and $R^{12}$=H, the radical $R^9$=phenyl, 4-methoxyphenyl, 4-methylphenyl, 4-nitrophenyl or p-benzaldehyde, the radicals $R^{10}$ and $R^{11}$ together=$(CH_2)_5$ and the radical $R^{20}$=$CH_3$ or
the radicals $R^3$ to $R^5$, $R^7$, $R^8$, $R^{12}$=H, the radical $R^6$=Br, the radical $R^9$=phenyl and the radicals $R^{10}$ and $R^{11}$ together=$(CH_2)_5$ or the radicals $R^3$ to $R^8$ and $R^{12}$=H, the radical $R^9$=phenyl or 4-methoxyphenyl and the radicals $R^{10}$ and $R^{11}$ together=$(CH_2)_5$ as the hydrochloride or the radical $R^3$=CO(OR$^{20}$), the radicals $R^4$ to $R^8$ and $R^{12}$=H, the radical $R^9$=phenyl, the radicals $R^{10}$ and $R^{11}$ together=$(CH_2)_5$ and the radical $R^{20}$=$CH_3$ as the hydrochloride and the enantiomers of the compound of formula I in which $R^1$=CH($R^9$)N($R^{10}$)($R^{11}$) and $R^2$=OR$^{12}$ and the radicals $R^3$ to $R^8$, $R^{12}$=H, $R^9$=phenyl and $R^{10}$ and $R^{11}$ together=$(CH_2)_5$, and the racemates of the compounds in which the radicals $R^1$=OR$^{12}$ and $R^2$=CH($R^9$)N($R^{10}$)($R^{11}$) and in each case the radicals $R^3$ to $R^8$ and $R^{12}$=H the radical $R^9$=phenyl, 2-bromophenyl, 3-bromophenyl or 4-bromophenyl and the radicals $R^{10}$ and $R^{11}$ together=$(CH_2)_5$ or $R^3$, $R^4$, $R^6$, $R^8$ and $R^{12}$=H, the radicals $R^5$, $R^7$=$CH_3$, or $R^5$=H and $R^7$=$CH_3$ the radical $R^9$=phenyl or 4-methoxyphenyl and the radicals $R^{10}$ and $R^{11}$ together=$(CH_2)_5$ or $R^3$ to $R^6$, $R^8$ and $R^{12}$=H, the radical $R^7$=$CH_3$, the radical $R^9$=4-methoxyphenyl or phenyl and the radicals $R^{10}$, $R^{11}$ together=$(CH_2)_5$.

2. The substituted 1- and 2-naphthol Mannich base according to claim 1, wherein at least one of the radicals $R^3$, $R^4$, $R^5$, $R^6$, $R^7$ or $R^8$ represents H.

3. The substituted 1- and 2-naphthol Mannich base according to claim 1, wherein at least one of the radicals $R^3$, $R^4$, $R^5$, $R^6$, $R^7$ or $R^8$ represents a $C_{1-6}$-alkyl radical.

4. The substituted 1- and 2-naphthol Mannich base according to claim 1, wherein at least one of the radicals $R^3$, $R^4$, $R^5$, $R^6$, $R^7$ or $R^8$ represents an aryl radical bonded via a $C_{1-2}$-alkylene group.

5. The substituted 1- and 2-naphthol Mannich base according to claim 1, wherein at least one of the radicals $R^3$, $R^4$, $R^5$, $R^6$, $R^7$ or $R^8$ represents F, Cl or Br.

6. The substituted 1- and 2-naphthol Mannich base according to claim 1, wherein at least one of the radicals $R^3$, $R^4$, $R^5$, $R^6$, $R^7$ or $R^8$ represents $SO_2NH_2$.

7. The substituted 1- and 2-naphthol Mannich base according to claim 1, wherein at least one of the radicals $R^3$, $R^4$, $R^5$, $R^6$, $R^7$ or $R^8$ represents NHR$^{13}$.

8. The substituted 1- and 2-naphthol Mannich base according to claim 1, wherein at least one of the radicals $R^3$, $R^4$, $R^5$, $R^6$, $R^7$ or $R^8$ represents CO($R^{22}$).

9. The substituted 1- and 2-naphthol Mannich base according to claim 1, wherein at least one of the radicals $R^3$, $R^4$, $R^5$, $R^6$, $R^7$ or $R^8$ represents OR$^{16}$.

10. The substituted 1- and 2-naphthol Mannich base according to claim 1, wherein at least one of the radicals $R^3$, $R^4$, $R^5$, $R^6$, $R^7$ or $R^8$ represents CO(OR$^{20}$).

11. The substituted 1- and 2-naphthol Mannich base according to claim 1, wherein the radical $R^9$ denotes an unsubstituted phenyl radical or a phenyl radical which is at least monosubstituted by $C_{1-4}$-alkyl, $C_{1-3}$-alkoxy, halogen, $CF_3$, CN, O-phenyl or OH.

12. The substituted 1- and 2-naphthol Mannich base according to claim 1, wherein the radical $R^{12}$ represents H.

13. The substituted 1- and 2-naphthol Mannich base according to claim 1, wherein the radical $R^{12}$ represents a $C_{1-6}$-alkyl radical.

14. The substituted 1- and 2-naphthol Mannich base according to claim 1, wherein the radical $R^{12}$ represents an aryl radical bonded via a $C_{1-2}$-alkylene group.

15. The substituted 1- and 2-naphthol Mannich base according to claim 1, wherein the radical $R^{13}$ represents H.

16. The substituted 1- and 2-naphthol Mannich base according to claim 1, wherein the radical $R^{13}$ represents a $C_{1-6}$-alkyl radical.

17. The substituted 1- and 2-naphthol Mannich base according to claim 1, wherein the radical $R^{13}$ represents an aryl radical bonded via a $C_{1-2}$-alkylene group.

18. The substituted 1- and 2-naphthol Mannich base according to claim 1, wherein the radical $R^{14}$ represents a $C_{1-6}$-alkyl radical.

19. The substituted 1- and 2-naphthol Mannich base according to claim 1, wherein the radical $R^{14}$ represents an aryl radical bonded via a $C_{1-2}$-alkylene group.

20. The substituted 1- and 2-naphthol Mannich base according to claim 1, wherein the radical $R^{15}$ represents a $C_{1-6}$-alkyl radical.

21. The substituted 1- and 2-naphthol Mannich base according to claim 1, wherein the radical $R^{15}$ represents an aryl radical bonded via a $C_{1-2}$-alkylene group.

22. The substituted 1- and 2-naphthol Mannich base according to claim 1, wherein the radical $R^{16}$ represents a $C_{1-6}$-alkyl radical.

23. The substituted 1- and 2-naphthol Mannich base according to claim 1, wherein the radical $R^{16}$ represents an aryl radical bonded via a $C_{1-2}$-alkylene group.

24. The substituted 1- and 2-naphthol Mannich base according to claim 1, wherein the radical $R^{16}$ represents H.

25. The substituted 1- and 2-naphthol Mannich base according to claim 1, wherein the radical $R^{16}$ represents CO($R^{17}$).

26. The substituted 1- and 2-naphthol Mannich base according to claim 1, wherein the radical $R^{17}$ represents a $C_{1-6}$-alkyl radical.

27. The substituted 1- and 2-naphthol Mannich base according to claim 1, wherein the radical $R^{17}$ represents an aryl radical bonded via a $C_{1-2}$-alkylene group.

28. The substituted 1- and 2-naphthol Mannich base according to claim 1, wherein the radical $R^{17}$ represents a phenyl radical which is optionally substituted by F, Cl, Br, $C_{1-4}$-alkyl or $C_{1-3}$-alkoxy.

29. The substituted 1- and 2-naphthol Mannich base according to claim 1, wherein the radical $R^{18}$ represents a $C_{1-6}$-alkyl radical.

30. The substituted 1- and 2-naphthol Mannich base according to claim 1, wherein the radical $R^{18}$ represents an aryl radical bonded via a $C_{1-2}$-alkylene group.

31. The substituted 1- and 2-naphthol Mannich base according to claim 1, wherein the radical $R^{18}$ represents a phenyl or naphthyl radical which is optionally substituted by F, Cl, Br, $C_{1-4}$-alkyl or $C_{1-3}$-alkoxy.

32. The substituted 1- and 2-naphthol Mannich base according to claim 1, wherein the radical $R^{20}$ represents a $C_{1-6}$-alkyl radical.

33. The substituted 1- and 2-naphthol Mannich base according to claim 1, wherein the radical $R^{20}$ represents an aryl radical bonded via a $C_{1-2}$-alkylene group.

34. The substituted 1- and 2-naphthol Mannich base according to claim 1, wherein the radical $R^{20}$ represents H.

35. The substituted 1- and 2-naphthol Mannich base according to claim 1, wherein the radical $R^{20}$ represents a phenyl radical which is optionally substituted by F, Cl, Br, $C_{1-4}$-alkyl or $C_{1-3}$-alkoxy.

36. The substituted 1- and 2-naphthol Mannich base according to claim 1, wherein the radical $R^{21}$ represents H.

37. The substituted 1- and 2-naphthol Mannich base according to claim 1, wherein the radical $R^{21}$ represents a $C_{1-6}$-alkyl radical.

38. The substituted 1- and 2-naphthol Mannich base according to claim 1, wherein the radical $R^{21}$ represents an aryl radical bonded via a $C_{1-2}$-alkylene group.

39. The substituted 1- and 2-naphthol Mannich base according to claim 1, wherein the radical $R^{22}$ represents H.

40. The substituted 1- and 2-naphthol Mannich base according to claim 1, wherein the radical $R^{22}$ represents a $C_{1-6}$-alkyl radical.

41. The substituted 1- and 2-naphthol Mannich base according to claim 1, wherein the radical $R^{22}$ represents an aryl radical bonded via a $C_{1-2}$-alkylene group.

42. The substituted 1- and 2-naphthol Mannich base according to claim 1, wherein the radical $R^{22}$ represents $NHNH_2$, $NHR^{18}$ or a phenyl radical which is optionally substituted by F, Cl, Br, $C_{1-4}$-alkyl or $C_{1-3}$-alkoxy.

43. The substituted 1- and 2-naphthol Mannich base according to claim 1 wherein the Mannich base is 4-chloro-2-(piperidin-1-yl-o-tolylmethyl)-naphthalen-1-ol, 4-chloro-2-[(2-chlorophenyl)-piperidin-1-yl-methyl]-naphthalen-1-ol, 5-amino-2-[(2-chlorophenyl)-piperidin-1-yl-methyl]-naphthalen-1-ol, 3-hydroxy-4-(piperidin-1-yl-o-tolylmethyl)-naphthalene-2-carboxylic acid hydrazide, 1-[(2-chlorophenyl)-piperidin-1-yl-methyl]-7-methoxynaphthalen-2-ol, 4-chloro-2-[(2-methoxyphenyl)-piperidin-1-yl-methyl]-naphthalen-1-ol, 6-bromo-1-[(2-methoxyphenyl)-piperidin-1-yl-methyl]-naphthalen-2-ol, 6-methoxy-1-[(2-methoxyphenyl)-piperidin-1-yl-methyl]-naphthalen-2-ol, 7-methoxy-1-[(2-methoxyphenyl)-piperidin-1-yl-methyl]-naphthalen-2-ol, 2-[(4-fluoro-phenyl)-pyrrolidin-1-yl-methyl]-naphthalen-1-ol.

44. A process for the preparation of one or more substituted 1- and 2-naphthol Mannich bases of formula I according to claim 1, wherein the radical $R^{12}$ represents H, said process comprising reacting one or more aromatic aldehyde compounds or aliphatic aldehyde compounds of formula II

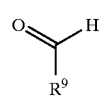

in which $R^9$ has the meaning according to formula I, in solution in the presence of a base, with one or more secondary amines of formula III

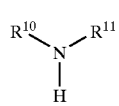

in which $R^{10}$ and $R^{11}$ have the meaning according to formula I, to give one or more aminal compounds of formula IV

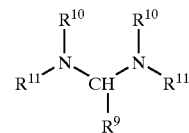

reacting said aminal compounds of formula IV without further purification, with an acid chloride in an absolute solvent to give one or more iminium salts of formula V

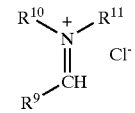

and reacting said iminium salts of formula V without further purification and in solution, with one or more substituted and/or unsubstituted 1- and 2-naphthol compounds of formula VI

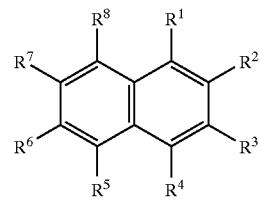

wherein $R^1$=H and $R^2$=OH or $R^1$=OH and $R^2$=H and in each case the radicals $R^3$ to $R^8$, $R^{13}$ to $R^{18}$ and $R^{20}$ to $R^{22}$ have the meaning according to formula I, and the 1- and 2-naphthol Mannich bases of formula I obtained in this way in which the radical $R^{12}$ represents H and the radicals $R^1$ to $R^{11}$, $R^{13}$ to $R^{18}$ and $R^{20}$ to $R^{22}$ have the meaning according to formula I are purified by extraction and are isolated by conventional methods.

45. A process for the preparation of one or more substituted 1- and 2-naphthol Mannich bases of formula I according to claim 1 wherein the radical $R^{12}$=$COR^{22}$, a $C_{1-10}$-alkyl, an aryl radical or an aryl radical bonded via a $C_{1-6}$-alkylene group, said process comprising reacting one or more aromatic aldehyde compounds or aliphatic aldehyde compounds of formula II

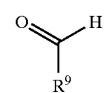

in which $R^9$ has the meaning according to formula I in solution in the presence of a base with one or more secondary amines of formula III

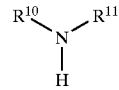

in which $R^{10}$ and $R^{11}$ have the meaning according to formula I, to give one or more aminal compounds of formula IV

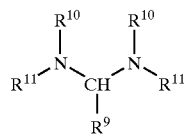

IV and reacting said aminal compounds of formula IV without further purification, with an acid chloride in an absolute solvent to give one or more iminium salts of formula V

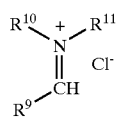

V and reacting said iminium salts of formula V without further purification and in solution, with one or more substituted and/or unsubstituted 1- and 2-naphthol compounds of formula VI

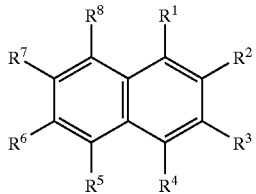

VI wherein $R^1$=H and $R^2$=OH or $R^1$=OH and $R^2$=H, and reacting the compounds of formula VI obtained in this way, wherein $R^1$=CH($R^9$)N($R^{10}$)($R^{11}$) and $R^2$=OH or $R^1$=OH and $R^2$=CH($R^9$)N($R^{10}$)($R^{11}$), in solution with compounds of formula $XR^{12'}$, wherein X=Cl, Br or I and $R^{12'}$=COR$^{22}$, a $C_{1-10}$-alkyl, an aryl radical or an aryl radical bonded via a $C_{1-6}$-alkylene group, in the presence of a base and the 1- and 2-naphthol Mannich bases of formula I obtained in this way, in which the radical $R^{12}$ represents COR$^{22}$, a $C_{1-10}$-alkyl, an aryl radical or an aryl radical bonded via a $C_{1-6}$-alkylene group, are purified by filtration and are isolated by conventional methods.

46. The process according to claim 45, wherein the reaction with the compounds of formula $XR^{12'}$ is carried out in dimethylformamide.

47. The process according to claim 45, wherein X=Cl.

48. The process according to claim 45, wherein the reaction with the compounds of formula $XR^{12'}$ is carried out in the presence of triethylamine or potassium tert-butylate as a base.

49. The process according to claim 45, wherein the compounds of formula I in which $R^{12}$ is not H, are purified by filtration over a scavenger resin.

50. The process according to claim 44, wherein the aromatic aldehyde compounds, and/or aliphatic aldehyde compounds of formula II are reacted in an organic solvent with one or more secondary amines of formula III.

51. The process according to claim 44, wherein the aromatic aldehyde compound and/or aliphatic aldehyde compounds of formula II are reacted in the presence of potassium carbonate or boric acid anhydride.

52. The process according to claim 44, wherein the aminal compounds of formula IV are reacted with acetyl chloride to give iminium salts of formula V.

53. The process according to claim 44, wherein the aminal compounds of formula IV are reacted in absolute diethyl ether to give iminium salts of formula V.

54. A medicament comprising, at least one substituted 1- and/or 2-naphthol Mannich base of formula I

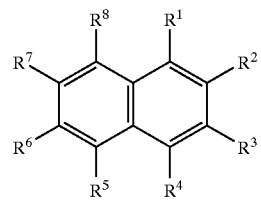

I wherein
$R^1$=CH($R^9$)N($R^{10}$)($R^{11}$) and $R^2$=OR$^{12}$ or
$R^1$=OR$^{12}$ and $R^2$=CH($R^9$)N($R^{10}$)($R^{11}$),
and in each case the radicals
$R^3$ to $R^8$ are identical or different and=H, F, Cl, Br, CF$_3$, CN, NO$_2$, SO$_2$NH$_2$, SO$_2$NHR$^{13}$, NHR$^{13}$, SR$^{15}$, OR$^{16}$, CO(OR$^{20}$), CH$_2$CO(OR$^{21}$), CO(R$^{22}$), a $C_{1-10}$-alkyl, an aryl radical or an aryl radical bonded via a $C_{1-6}$-alkylene group,
$R^9$ denotes an aryl radical or an alkyl radical without an acid proton in the α-position,
or $R^{10}$ and $R^{11}$ together denote (CH$_2$)$_n$, where n is 4 or 5,
$R^{12}$=H, COR$^{22}$, a $C_{1-10}$-alkyl, an aryl radical or an aryl bonded via a $C_{1-6}$-alkylene group,
$R^{13}$=H, COR$^{14}$, a $C_{1-10}$-alkyl, an aryl radical or an aryl bonded via a $C_{1-6}$-alkylene group,
$R^{14}$=H, a $C_{1-10}$-alkyl, an aryl radical or an aryl bonded via a $C_{1-6}$-alkylene group,
$R^{15}$=H, a $C_{1-10}$-alkyl, an aryl radical or an aryl bonded via a $C_{1-6}$-alkylene group,
$R^{16}$=H, CO($R^{17}$), a $C_{1-10}$-alkyl, an aryl radical or an aryl bonded via a $C_{1-6}$-alkylene group,
$R^{17}$=H, a $C_{1-10}$-alkyl, an aryl radical or an aryl bonded via a $C_{1-6}$-alkylene group,
$R^{18}$=H, a $C_{1-10}$-alkyl, an aryl radical or an aryl bonded via a $C_{1-6}$-alkylene group,
$R^{20}$=H, a $C_{1-10}$-alkyl, an aryl radical or an aryl bonded via a $C_{1-6}$-alkylene group,
$R^{21}$=H, a $C_{1-10}$-alkyl, an aryl radical or an aryl bonded via a $C_{1-6}$-alkylene group,
$R^{22}$=H, NHNH$_2$, NHR$^{18}$, a $C_{1-10}$-alkyl, an aryl radical or an aryl bonded via a $C_{1-6}$-alkylene group,
or a racemate, enantiomer, diastereomer, a corresponding base of a physiologically tolerated acid or a corresponding salt of a physiologically tolerated acid, and optionally further active compounds or auxiliary substances thereof.

55. The medicament according to claim 54, comprising a mixture of enantiomers of at least one substituted 1-naphthol Mannich base and/or 2-naphthol Mannich base of formula I in non-equimolar amounts.

56. The medicament according to claim 55, wherein the relative proportion of one of the enantiomers of the mixture is 5 to 45 mol %, based on the mixture of enantiomers.

57. The substituted 1- and 2-naphthol Mannich base according to claim 11, wherein the radical $R^9$ is 2-methoxy-phenyl, 3-methoxy-phenyl, 4-methoxy-phenyl, 2-methyl-phenyl, 3-methyl-phenyl, 4-methyl-phenyl, 2-tert-butylphenyl, 3-tert-butyl-phenyl, 4-tert-butylphenyl, 2-fluoro-phenyl, 3-fluoro-phenyl, 4-fluorophenyl, 2-chloro-phenyl, 3-chloro-phenyl, 4-chlorophenyl, 2-bromo-phenyl, 3-bromo-phenyl, 4-bromophenyl, 5-bromo-2-fluoro-phenyl, 2-chloro-fluorophenyl, 2-chloro-5-fluoro-phenyl, 2-chloro-6-fluorophenyl, 4-bromo-2-fluoro-phenyl, 3-bromo-4-fluorophenyl, 3-bromo-2-fluoro-phenyl, 2,3-dichloro-phenyl, 2,4-dichloro-phenyl, 2,5-dichlorophenyl, 3,4-dichlorophenyl, 2,3-dimethyl-phenyl, 2,4-dimethyl-phenyl, 2,5-dimethylphenyl, 2,3-dimethoxy-phenyl, 2,4-dimethoxyphenyl, 2,5-dimethoxy-phenyl, 3,4-dimethoxy-phenyl, 3,4,5-trimethoxy-phenyl, 2-trifluoromethyl-phenyl, 3-trifluoromethyl-phenyl or 4-trifluoromethyl-phenyl radical.

58. The substituted 1- and 2-naphthol Mannich base according to claim 11, wherein $R^9$ is an unsubstituted phenyl radical.

59. The substituted 1- and 2-naphthol Mannich base according to claim 31, wherein $R^{18}$ is a phenyl radical which is optionally substituted by F, Cl, Br, $C_{1-4}$-alkyl or $C_{1-3}$-alkoxy.

60. The process of claim 44, wherein the aromatic aldehyde compounds or aliphatic aldehyde compounds of formula II are reacted at a temperature of from $-10°$ C. to $110°$ C.

61. The process of claim 44, wherein the iminium salts of formula V are reacted in acetonitrile.

62. The process of claim 45, wherein the aromatic aldehyde compounds and/or aliphatic aldehyde compounds of formula II are reacted at a temperature of from $-10$ to $110°$ C.

63. The process of claim 45, wherein the iminium salts of formula V are reacted in acetonitrile.

64. The process of claim 45, wherein the iminium compounds of formula $XR^{12'}$ are reacted at a temperature of from 10 to $150°$ C.

65. The process of claim 49, wherein the scavenger resin is polymer-bonded tris(2-aminoethyl)amine and/or 3-(3-mercaptophenylpropane-amidomethylpolystyrene.

66. The process according to claim 50, wherein the compounds are reacted in toluene.

67. The process according to claim 45, wherein the aromatic aldehyde compounds or aliphatic aldehyde compounds of formula II are reacted in the presence of potassium carbonate or boric acid anhydride as a base.

68. The process according to claim 45, wherein one or more aromatic aldehyde compounds or aliphatic aldehyde compounds of formula II are reacted in an organic solvent with one or more secondary amines of formula III.

69. The process according to claim 68, wherein the compounds are reacted in toluene.

70. The process according to claim 42, wherein $R^{22}$ is $NHNH_2$ or $NHR^{18}$.

71. The process of claim 45, wherein the aminal compounds of formula IV are reacted with acetyl chloride to give iminium salts of formula V.

72. The process of claim 45, wherein the aminal compounds of formula IV are reacted in absolute diethyl ether to give iminium salts of formula V.

73. The medicament of claim 54, wherein $R^3$ to $R^8$ are identical or different and may be H, F, Cl, Br, $SO_2NH_2$, $NHR^{13}$, $CO(R^{22})$, $OR^{16}$, $CO(OR^{20})$, a $C_{1-6}$-alkyl radical or an aryl radical bonded by a $C_{1-2}$-alkylene group.

74. The medicament of claim 54, wherein $R^3$ to $R^8$ are identical or different and may be H, $NHR^{13}$, $CO(R^{22})$, $OR^{16}$ or $CO(OR^{20})$.

75. The medicament of claim 54, wherein $R^9$ is an unsubstituted phenyl radical or a phenyl radical which is at least monosubstituted by $C_{1-4}$-alkyl, $C_{1-3}$-alkoxy, halogen, $CF_3$, CN, O-phenyl or OH.

76. The medicament of claim 54, wherein $R^9$ is 2-methoxy-phenyl, 3-methoxy-phenyl, 4-methoxy-phenyl, 2-methyl-phenyl, 3-methyl-phenyl, 4-methyl-phenyl, 2-tert-butyl-phenyl, 3-tert-butylphenyl, 4-tert-butyl-phenyl, 2-fluoro-phenyl, 3-fluoro-phenyl, 4-fluoro-phenyl, 2-chloro-phenyl, 3-chloro-phenyl, 4-chloro-phenyl, 2-bromo-phenyl, 3-bromo-phenyl, 4-bromo-phenyl, 5-bromo-2-fluoro-phenyl, 2-chloro-4-fluoro-phenyl, 2-chloro-5-fluoro-phenyl, 2-chloro-6fluoro-phenyl, 4-bromo-2-fluoro-phenyl, 3-bromo-4-fluoro-phenyl, 3-bromo-2-fluoro-phenyl, 2,3-dichloro-phenyl, 2,4-dichloro-phenyl, 2,5-dichlorophenyl, 3,4-dichlorophenyl, 2,3-dimethylphenyl, 2,4-dimethyl-phenyl, 2,5-dimethylphenyl, 2,3-dimethoxy-phenyl, 2,4-dimethoxy-phenyl, 2,5-dimethoxyphenyl, 3,4-dimethoxy-phenyl, 3,4,5-trimethoxy-phenyl, 2-trifluoromethyl-phenyl, 3-trifluoromethyl-phenyl or 4-trifluoromethyl-phenyl radical.

77. The medicament of claim 54, wherein $R^9$ is an unsubstituted phenyl radical.

78. The medicament of claim 54, wherein $R^{12}$ is H, a $C_{1-6}$-alkyl radical or an aryl radical bonded via a $C_{1-2}$-alkylene group.

79. The medicament of claim 54, wherein $R^{13}$ is H, a $C_{1-6}$-alkyl radical or an aryl radical bonded via a $C_{1-2}$-alkylene group.

80. The medicament of claim 54, wherein $R^{13}$ is H.

81. The medicament of claim 54, wherein $R^{14}$ is a $C_{1-6}$-alkyl radical or an aryl radical bonded via a $C_{1-2}$-alkylene group.

82. The medicament of claim 54, wherein $R^{15}$ is a $C_{1-6}$-alkyl radical or an aryl radical bonded via a $C_{1-2}$-alkylene group.

83. The medicament of claim 54, wherein $R^{16}$ is H, a $C_{1-6}$-alkyl radical, an aryl radical bonded via a $C_{1-2}$-alkylene group or $CO(R^{17})$.

84. The medicament of claim 54, wherein $R^{16}$ is H or $CO(R^{17})$.

85. The medicament of claim 54, wherein $R^{17}$ is a $C_{1-6}$-alkyl radical, an aryl radical bonded via a $C_{1-2}$-alkylene group or a phenyl radical which is optionally substituted by F, Cl, Br, $C_{1-4}$-alkyl or $C_{1-3}$-alkoxy.

86. The medicament of claim 54, wherein $R^{17}$ is a phenyl radical which is optionally substituted by F, Cl, Br, $C_{1-4}$-alkyl or $C_{1-3}$-alkoxy.

87. The medicament of claim 54, wherein $R^{18}$ is a $C_{1-6}$-alkyl radical, an aryl radical bonded via a $C_{1-2}$-alkylene group or a phenyl or naphthyl radical which is optionally substituted by F, Cl, Br, $C_{1-4}$-alkyl or $C_{1-3}$-alkoxy.

88. The medicament of claim 54, wherein $R^{18}$ is a phenyl radical which is optionally substituted by F, Cl, Br, $C_{1-4}$-alkyl or $C_{1-3}$-alkoxy.

89. The medicament of claim 54, wherein $R^{20}$ is H, a $C_{1-6}$-alkyl radical, an aryl radical bonded via a $C_{1-2}$-alkylene group or a phenyl radical which is optionally substituted by F, Cl, Br, $C_{1-4}$-alkyl or $C_{1-3}$-alkoxy.

90. The medicament of claim 54, wherein $R^{20}$ is H or a phenyl radical which is optionally substituted by F, Cl, Br, $C_{1-4}$-alkyl or $C_{1-3}$-alkoxy.

91. The medicament of claim 54, wherein $R^{21}$ is H, a $C_{1-6}$-alkyl radical or an aryl radical bonded via a $C_{1-2}$-alkylene group.

92. The medicament of claim 54, wherein $R^{22}$ is H, a $C_{1-6}$-alkyl radical, an aryl radical bonded via a $C_{1-2}$-alkylene group, $NHNH_2$, $NHR^{18}$ or a phenyl radical which is optionally substituted by F, Cl, Br, $C_{1-4}$-alkyl or $C_{1-3}$-alkoxy.

93. The medicament of claim 54, wherein $R^{22}$ is $NHNH_2$, $NHR^{18}$ or a phenyl radical which is optionally substituted by F, Cl, Br, $C_{1-4}$-alkyl or $C_{1-3}$-alkoxy.

94. The medicament of claim 54, wherein $R^{22}$ is $NHNH_2$ or $NHR^{18}$.

95. The medicament of claim 56, wherein in the reactive portion of one of the enantiomers of the mixture is 10–40 mol % based on the mixture of enantiomers.

96. A process for preparing a pharmaceutical composition, said process comprising mixing the medicament of claim 54 with a pharmaceutically acceptable carrier or diluent.

97. A method comprising administering a composition comprising at least one Mannich base of claim 1 in an amount effective for combating pain in a person in need thereof.

98. A method comprising administering composition comprising at least one Mannich base of claim 1 in an amount effective for treating inflammatory reactions in a person in need thereof.

99. A method comprising administering a composition comprising one or more Mannich base of claim 1 in an amount effective for treating allergic reactions to a person in need thereof.

100. A method comprising administering a composition comprising at least one Mannich base of claim 1 in an amount effective for treating drug and/or alcohol abuse in a person in need thereof.

101. A method comprising administering a composition comprising at least one Mannich base of claim 1 in an amount effective for treating diarrhea to a person in need thereof.

102. A method comprising administering a composition comprising at least one Mannich base of claim 1 in an amount effective for treating gastritis to a person in need thereof.

103. A method comprising administering a composition comprising at least one Mannich base of claim 1 in an amount effective for treating ulcers to a person in need thereof.

104. A method comprising administering a composition comprising at least one Mannich base of claim 1 in an amount effective for treating cardiovascular disease to a person in need thereof.

105. A method comprising administering a composition comprising at least one Mannich base of claim 1 in an amount effective for treating urinary incontinence to a person in need thereof.

106. A method comprising administering a composition comprising at least one Mannich base of claim 1 in an amount effective for treating depression to a person in need thereof.

107. A method comprising administering a composition comprising at least one Mannich base of claim 1 in an amount effective for treating shock to a person in need thereof.

108. A method comprising administering a composition comprising at least one Mannich base of claim 1 in an amount effective for treating migraines to a person in need thereof.

109. A method comprising administering a composition comprising at least one Mannich base of claim 1 in an amount effective for treating narcolepsy to a person in need thereof.

110. A method comprising administering a composition comprising at least one Mannich base of claim 1 in an amount effective for reducing the weight of a person.

111. A method comprising administering a composition comprising at least one Mannich base of claim 1 in an amount effective for treating asthma to a person in need thereof.

112. A method comprising administering a composition comprising at least one Mannich base of claim 1 in an amount effective for treating glaucoma to a person in need thereof.

113. A method comprising administering a composition comprising at least one Mannich base of claim 1 in an amount effective for treating hyperkinetic syndrome to a person in need thereof.

* * * * *